(12) United States Patent
Compton et al.

(10) Patent No.: US 11,964,237 B2
(45) Date of Patent: *Apr. 23, 2024

(54) MOLECULAR WEIGHT FILTRATION SYSTEM AND APPARATUS WITH ADDITIONAL FLOW CONFIGURATIONS

(71) Applicant: Integrated Protein Technologies, Inc., Evanston, IL (US)

(72) Inventors: Philip D. Compton, Chicago, IL (US); Jared Drader, San Marcos, CA (US)

(73) Assignee: Integrated Protein Technologies, Inc., Evanston, IL (US)

( * ) Notice: Subject to any disclaimer, the term of this patent is extended or adjusted under 35 U.S.C. 154(b) by 188 days.

This patent is subject to a terminal disclaimer.

(21) Appl. No.: 17/693,155

(22) Filed: Mar. 11, 2022

(65) Prior Publication Data

US 2022/0193616 A1      Jun. 23, 2022

Related U.S. Application Data

(63) Continuation-in-part of application No. 17/410,750, filed on Aug. 24, 2021, and a continuation-in-part of application No. 17/096,146, filed on Nov. 12, 2020, which is a continuation-in-part of application No. 16/193,539, filed on Nov. 16, 2018, now Pat. No. 10,864,483.

(51) Int. Cl.
*B01D 63/08* (2006.01)
*B01D 69/02* (2006.01)
*G01N 1/40* (2006.01)

(52) U.S. Cl.
CPC ......... *B01D 63/087* (2013.01); *B01D 63/082* (2013.01); *B01D 69/02* (2013.01); *G01N 1/4005* (2013.01); *B01D 2313/025* (2013.01); *B01D 2313/04* (2013.01); *B01D 2313/08* (2013.01); *B01D 2313/10* (2013.01); *B01D 2313/13* (2013.01); *B01D 2313/20* (2013.01); *B01D 2313/50* (2013.01); *B01D 2313/54* (2013.01); *B01D 2313/56* (2013.01); *B01D 2313/58* (2013.01); *B01D 2317/02* (2013.01); *B01D 2317/08* (2013.01); *B01D 2325/20* (2013.01); *B01D 2325/34* (2013.01)

(58) Field of Classification Search
CPC .... B01D 63/087; B01D 63/082; B01D 69/02; B01D 2313/025; B01D 2313/54; B01D 2313/56; B01D 2313/58; B01D 2317/08; G01N 1/4005; C12N 15/1017
See application file for complete search history.

(56) References Cited

U.S. PATENT DOCUMENTS 10,864,483 B2 * 12/2020 Compton ............... B01D 69/02
2004/0219072 A1 * 11/2004 Yamakawa ....... B01L 3/502753
422/400

(Continued)

*Primary Examiner* — David Z Huang
(74) *Attorney, Agent, or Firm* — Anooj Patel; Heber Martin Carbajal; Hankin Patent Law, APC

(57) ABSTRACT

A molecular filtration device and method of use capable of filtering and purifying molecules of a particular characteristic, wherein the amount of molecule to be filtered may be in the nanogram range and may be dispersed in a relatively large volume of solution. The resultant elution may include a relatively high concentration of desired molecule, due to a relatively small volume.

17 Claims, 35 Drawing Sheets

(56) References Cited

U.S. PATENT DOCUMENTS

| | | | |
|---|---|---|---|
| 2005/0191530 A1* | 9/2005 | Mossman | H01M 8/04119 429/414 |
| 2016/0003787 A1* | 1/2016 | Wright | G01N 30/7266 250/288 |
| 2018/0104650 A1* | 4/2018 | Kamito | B01D 63/087 |

* cited by examiner

MOLECULAR WEIGHT FILTRATION SYSTEM AND APPARATUS WITH ADDITIONAL FLOW CONFIGURATIONS

CROSS-REFERENCE TO RELATED APPLICATIONS

This application is a Continuation-In-Part of U.S. Non-Provisional application Ser. No. 17/096,146, filed on Nov. 12, 2020, entitled "FRIT FOR USE WITH MOLECULAR WEIGHT FILTRATION SYSTEM AND APPARATUS", which is a Continuation-In-Part of U.S. Non-Provisional application Ser. No. 16/193,539, now U.S. Pat. No. 10,864,483, filed on Nov. 16, 2018, entitled "MOLECULAR WEIGHT FILTRATION SYSTEM AND APPARATUS", the contents of which are incorporated herein by reference as thought set forth in their entirety.

This application is also a Continuation-In-Part of U.S. Non-Provisional application Ser. No. 17/410,750, filed on Aug. 24, 2021, entitled "HOUSED CONSUMABLE FOR USE WITH MOLECULAR WEIGHT FILTRATION SYSTEM AND APPARATUS", the contents of which are incorporated herein by reference as thought set forth in their entirety.

FIELD OF USE

This disclosure pertains to a system and apparatus for filtration, purification, and concentration of biological molecules based on the molecules' molecular weight cut-off. More particularly, the system and apparatus may comprise a system for proteomics sample preparation, wherein the sample size is extremely small, even as small as being in the nanogram range, and subsequently directly processed by molecule analytic techniques.

BACKGROUND

Obtaining a sufficiently pure sample of biological molecules such as DNA, RNA, and proteins for purposes of experimentation can be a difficult task but is often a required step to performing a wide array of experiments.

The process generally begins with a scientist performing a synthesis step to generate the molecules desired. The molecules desired may be DNA, RNA, proteins, or other large molecules.

In some embodiments a plasmid containing genetic code to synthesize a specific protein may be inserted into microbial cells. The plasmid may also contain a specific antibiotic resistance, such that any microbial cells that did not receive the plasmid successfully may be eliminated by an antibiotic. A single colony of the microbial cells may then be selected, transferred to a growth medium, and grown until a desired cell density is obtained. Next, an activator molecule may be added to the growth medium to cause the microbial cells to produce the desired protein. The microbial cells, at that stage, will contain within them the specific protein in addition to all the other components of the cells. At that stage, various filtration and purification techniques may be used to isolate the specific protein. Alternatively, samples may be prepared from endogenous material, such as human tissue homogenates or human blood cell lysates.

One filtration and concentration technique, dead end filtration, allows a solution containing the specific protein to be concentrated while simultaneously removing other components of the solution that are smaller than a molecular weight cut off ("MWCO") of a membrane at the end of the dead end filtration device. While this may be an effective technique for concentrating and removing smaller contaminants, this technique may often cause the membrane to become clogged and slow down. Dead end filtration also often accepts only small amount of solution at a time, so the scientist may need to repeatedly refill the dead end filtration device with solution containing the specific protein.

Another filtration and concentration technique, cross flow filtration, allows for the scientist to feed a large amount of solution without needing to stop and refill periodically by continually causing the solution to flow across a membrane, such that solution and contaminants pass through the membrane, while the solution and large molecules do not pass through the membrane. After the solution passes over the membrane, it may be recycled for further purification. Over time, as solution and contaminants pass through the membrane, but the specific protein does not, the concentration of the specific protein increases.

Most existing techniques for purification of molecules are directed towards relatively large sample sizes. Scientists often face difficulty in effectively isolating and purifying molecules at relatively low sample sizes, such as at the nanogram scale. Scientists may need to operate with these extremely small sample sizes for many reasons. Some reasons may be that the sample utilizes a radioactive isotope, the sample may interact with itself, or the sample is difficult to produce at all.

Current systems and apparatus for filtration of extremely small sample sizes often require individuals to manually insert components for filtration, such as membranes, into structures and manually secure those components. Additionally, membranes used in molecular filtration have a limited lifespan and must be changed fairly regularly to ensure minimal cross contamination and structural integrity of the membrane after substantial use.

For example, the molecular filtration device described in U.S. Pat. No. 10,864,483 allows for filtration of extremely small sample sizes, but requires a user to manually separate a lower and upper portion and manually position a membrane to create a channel within which solution may be filtered. This may be a time consuming process, and allows for the introduction of human error in the set-up process. Furthermore, this methodology limits the amount and type of data that may be collected automatically by the device itself by requiring the user to specifically record the data by hand. Additionally, the user must keep track of membrane usage manually in this disclosure.

Accordingly, what is needed is a membrane in a housing that can be used to streamline manual insertion or set-up of membrane devices when used with a system or apparatus that effectively filter, purify, and concentrate a desired biological molecule.

SUMMARY

To minimize the limitations in the prior art, and to minimize other limitations that will become apparent upon reading and understanding the present specification, the present invention is directed to a consumable device for use with molecular filtration devices and systems.

The contents of this summary section are provided only as a simplified introduction to the disclosure and are not intended to be used to limit the scope of the claims. These, as well as other components, steps, features, objects, benefits, and advantages, will now become clear from a review of the following detailed description of illustrative embodiments, and of the claim.

BRIEF DESCRIPTION OF THE DRAWINGS

The drawings show illustrative embodiments, but do not depict all embodiments. Other embodiments may be used in addition to or instead of the illustrative embodiments. Details that may be apparent or unnecessary may be omitted for the purpose of saving space or for more effective illustrations. Some embodiments may be practiced with additional components or steps and/or without some or all components or steps provided in the illustrations. When different drawings contain the same numeral, that numeral refers to the same or similar components or steps.

DETAILED DESCRIPTION OF THE ILLUSTRATIVE EMBODIMENTS

Figure 1:
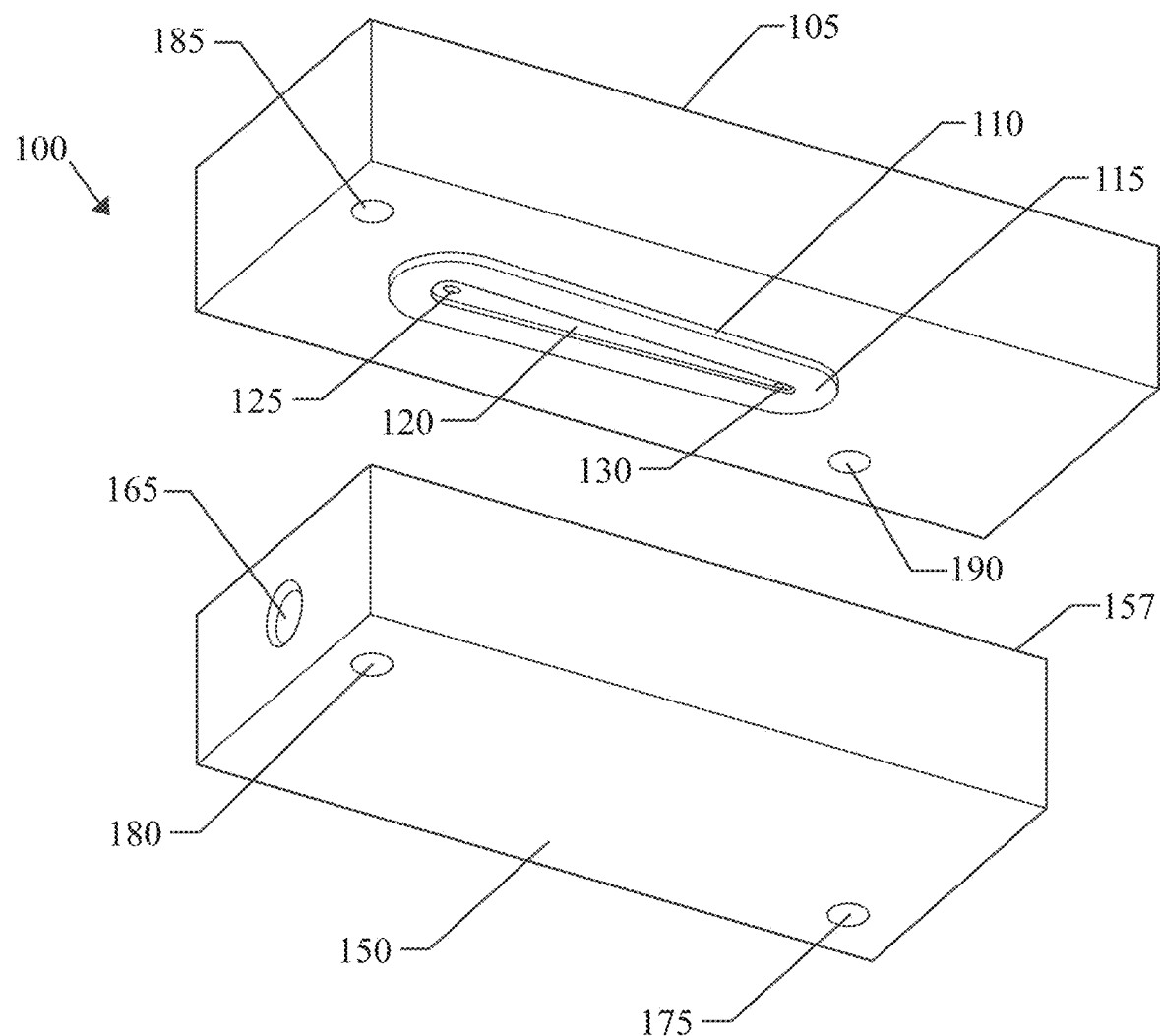
FIG. 1 is an illustration of a perspective view of one embodiment of a molecular filtration device.

Before the present device, methods, and systems are disclosed and described, it is to be understood that the methods and systems are not limited to specific device and methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that may be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all embodiments of this application including, but not limited to, steps in disclosed methods. Thus, if there are a variety of additional steps that may be performed it is understood that each of these additional steps may be performed with any specific embodiment or combination of embodiments of the disclosed methods.

The present methods and systems may be understood more readily by reference to the following detailed description of preferred embodiments and the examples included therein and to the Figures and their previous and following description.

In the following description, certain terminology is used to describe certain features of one or more embodiments. For purposes of the specification, unless otherwise specified, the term "substantially" refers to the complete or nearly complete extent or degree of an action, characteristic, property, state, structure, item, or result. For example, in one embodiment, an object that is "substantially" located within a housing would mean that the object is either completely within a housing or nearly completely within a housing. The exact allowable degree of deviation from absolute completeness may in some cases depend on the specific context. However, generally speaking, the nearness of completion will be so as to have the same overall result as if absolute and total completion were obtained. The use of "substantially" is also equally applicable when used in a negative connotation to refer to the complete or near complete lack of an action, characteristic, property, state, structure, item, or result.

As used herein, the terms "approximately" and "about" generally refer to a deviance of within 5% of the indicated number or range of numbers. In one embodiment, the term "approximately" and "about", may refer to a deviance of between 0.001-10% from the indicated number or range of numbers.

As used herein, "ul" refers to microliter, "ml" refers to milliliter, and "ng" refers to nanogram.

Various embodiments are now described with reference to the drawings. In the following description, for purposes of explanation, numerous specific details are set forth in order to provide a thorough understanding of one or more embodiments. It may be evident, however, that the various embodiments may be practiced without these specific details. In other instances, well-known structures and devices are shown in block diagram form to facilitate describing these embodiments.

Various embodiments presented in terms of systems may comprise a number of components, modules, and the like. It is to be understood and appreciated that the various systems may include additional components, modules, etc. and/or may not include all of the components, modules, etc. discussed in connection with the figures. A combination of these approaches may also be used.

Figure 3:
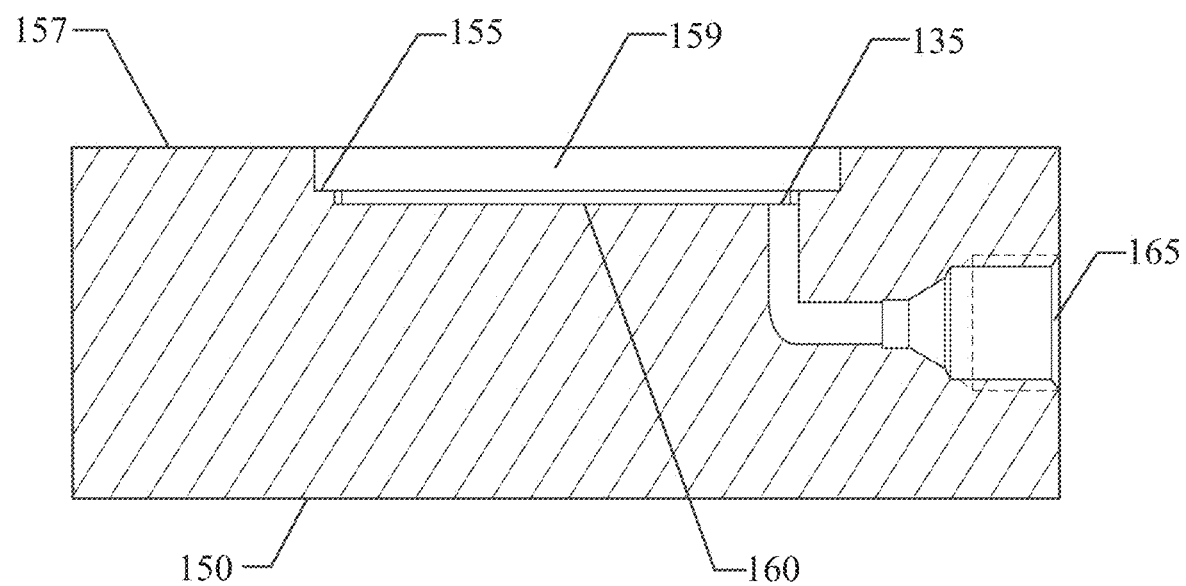
FIG. 3 is an illustration of a cross-sectional view of one embodiment of a lower portion of the molecular filtration device.
Figure 4:
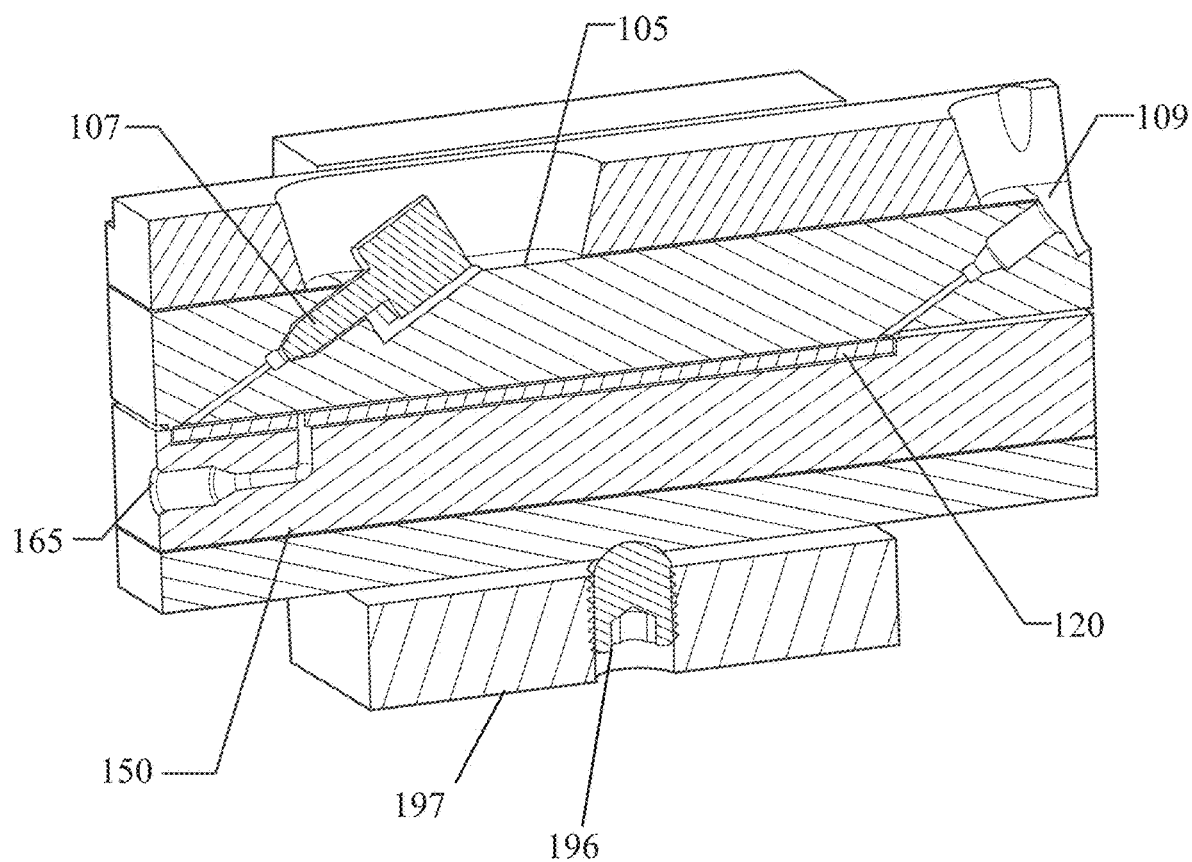
FIG. 4 is an illustration of a cross-sectional view of one embodiment of the upper portion and lower portion of the molecular filtration device in an assembled configuration.
Figure 5:
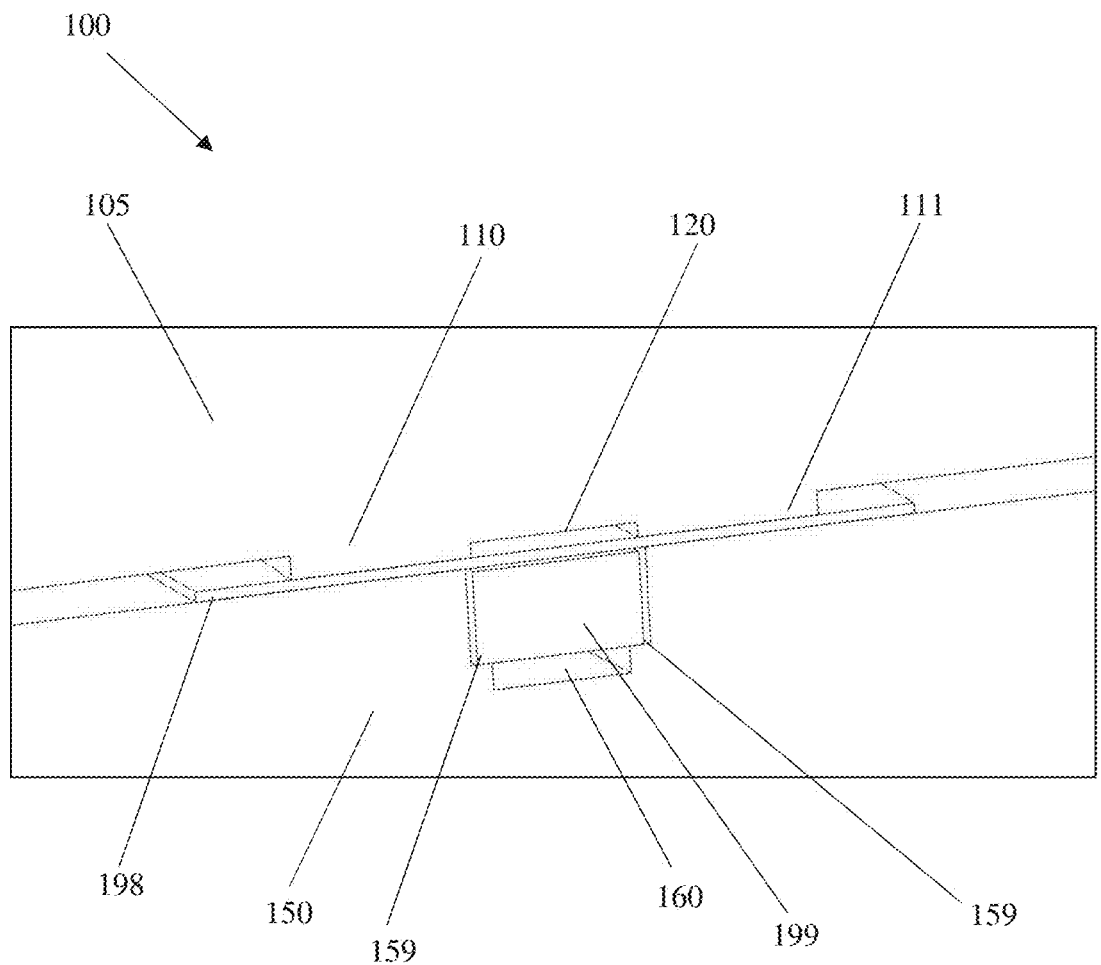
FIG. 5 is an illustration of a cross-sectional view of one embodiment of the molecular filtration device including a frit.

FIG. 1 is an illustration of one embodiment of a molecular filtration device. As shown in FIG. 1, the molecular filtration device 100 may comprise an upper portion 105 and a lower portion 150. The upper portion 105 may comprise a first upper port 125, second upper port 130, channel forming lip 110, and upper securing structures 185, 190. The lower portion 150 may comprise an upper sealing surface 157, a lower port 165, and lower securing structures 175, 180. As shown in FIGS. 3-5, detailed more fully herein below, the lower portion 150 may also comprise a frit portion 159, frit supporting lip 155 (as shown in FIG. 3), and reservoir 160.

The first upper port 125 and second upper port 130 may be configured to receive solution flow devices, wherein the solution flow devices may be connected to pumps through solution transfer structures such that each of the flow devices may be able to independently adjust the flow rate through the upper ports 125, 130, including reversing the flow direction of the solution. For example, the flow of solution may be such that the solution is ejected from the first upper port 125 and taken up by the second upper port 130. Alternatively, solution may be ejected from both the first and second upper ports 125, 130.

Similar to the first and second upper ports 125, 130, the lower port 165 may be configured to receive a lower flow device configured to inject or withdraw solution from the reservoir 160. As used herein, the terms inject and withdraw do not necessarily denote the mechanism for causing flow of solution, but rather are used to denote the direction of flow of solution.

The channel forming lip 110 may be a protrusion of the upper portion 105 comprising a lower sealing surface 115. The channel forming lip 110 may comprise a channel forming cavity 120, wherein when the lower sealing surface 115 of the upper portion 105 and the upper sealing surface 157 of the lower portion 150 are engaged with a membrane in between them, such that the channel forming cavity 120 forms a channel.

The first and second upper ports 125, 130 may allow for the flow of solution into and/or through the channel formed by channel forming cavity 120, depending on the direction of the flow of solution through the first and second upper ports 125, 130.

In a preferred configuration, a membrane may be placed and secured between the upper sealing surface 157 of the lower portion 150 and lower sealing surface 115 of the upper portion 105 when the upper sealing surface 157 and lower sealing surface 115 are fitted together and engaged. The membrane may allow for molecules of a certain size or characteristic to pass through, while preventing other, often larger, molecules from passing through the membrane. The membrane may be subjected to relatively high pressure due to the upper ports 125, 130 injecting liquid into the channel, with pressures reaching as high as 1,500 psig, or as low as 0 psig. Generally, the higher the pressure that is applied to the membrane, the faster the solution may pass through the membrane, provided the membrane is not structurally compromised by the higher pressure. One method of increasing the maximum operational pressure for the membrane is to provide the membrane with an additional rigid support structure, such as a frit.

In b embodiment, the first and second upper ports 125, 130 may be configured to inject a solution comprising desired molecules for isolation and purification, along with other, non-desired molecules, into the channel formed by the membrane and the channel forming cavity 120. As solution is injected into the channel formed by the membrane and the channel forming cavity 120, pressure increases, and the solution, along with molecules capable of passing through the membrane, may pass through the membrane, thereby passing into the reservoir 160 (shown in FIG. 3) and then out through the lower port 165. After a desired amount of the solution has passed through the membrane, the desired molecules may be concentrated in the channel formed by the membrane and the channel forming cavity 120, and on the membrane. In order to elute the desired molecules, the flow direction of the second upper port 130 and the lower port 165 may be reversed, such that the solution may be injected into the reservoir 160 and the channel formed by the membrane and the channel forming cavity 120 through the lower port 165 and first upper port 125, respectively, and the solution may be eluted from the second upper port 130. Alternatively, the first upper port 125 may allow for no flow, such that flow is solely from the lower port 165 to the second upper port 130. By this process, the solution having the desired molecule may be eluted through the second upper port 130 in a relatively small volume of solution or buffer.

In a preferred embodiment, very dilute amounts of molecules in relatively large volumes may be pushed through the first and second upper ports 125, 130 until substantially all of the desired molecules are in the channel formed by the membrane and the channel forming cavity 120. A buffer solution having a desired characteristic may then be run through the first and second upper ports 125, 130 in order to wash the desired molecule and ensure that all of the non-desired molecules capable of passing through the membrane are passed through the membrane, such as into a waste container. At that point the now concentrated and purified desired molecules may be retrieved through the second upper port 130. A buffer container may then be connected to the lower port 165 to inject a buffer into the reservoir 160, such that the desired molecule in the buffer solution is eluted into the second upper port 130 for collection and further use.

The upper portion 105 and lower portion 150 may be made of stainless steel, or other material of suitable strength and general non-reactivity. The membrane may be made of regenerated cellulose, polyether sulfone, cellulose acetate or other material that may create pore sizes of defined size and distribution.

Figure 2:
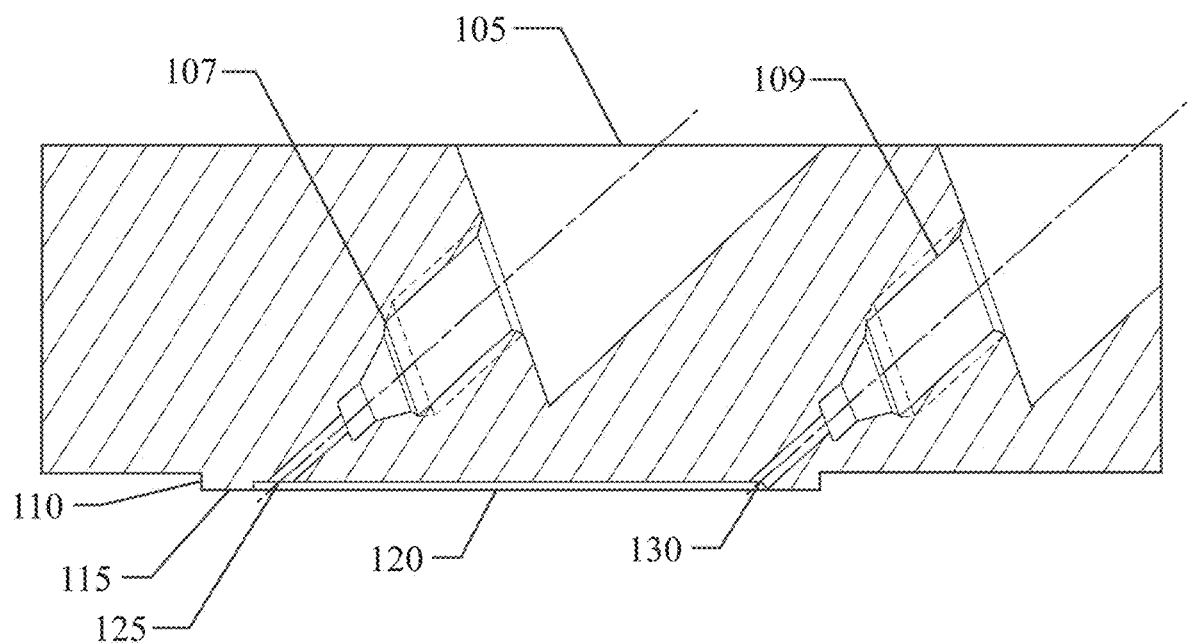
FIG. 2 is an illustration of a cross-sectional view of one embodiment of an upper portion of the molecular filtration device.

FIG. 2 is an illustration of a cross-sectional view of one embodiment of an upper portion of the molecular filtration device. As shown in FIG. 2, the first upper flow device 107 and second upper flow device 109 may be configured to engage the first upper port 125 and second upper port 130, respectively. The channel forming cavity 120 may be extremely small in volume relative to the upper portion 105. The channel forming cavity 120 may be about 5 uL to about 50 uL. In one embodiment, the channel forming cavity 120 may be about 14.6 uL.

FIG. 3 is an illustration of a cross-sectional view of one embodiment of a lower portion of the molecular filtration device. As shown in FIG. 3, the lower portion 150 may comprise an upper sealing surface 157, top end of lower port 135, frit receiving portion 159, frit supporting lip 155, and reservoir 160. The lower end of lower port 165 may be configured to receive a lower flow device.

FIG. 4 is an illustration of a cross-sectional view of one embodiment of the upper portion and lower portion of the molecular filtration device in an assembled configuration. As shown in FIG. 4, the first upper flow device 107 and second upper flow device 109 may be angled relative to the channel forming cavity 120. In one embodiment, the upper flow devices 107, 109 may be between 15 and 165 degrees relative to the bottom surface of the upper portion 105.

The molecular filtration device 100 may also comprise a pressure application mechanism 197, which may be configured to apply a force such that the upper portion 105 and lower portion 150 are pressed toward one another. This pressure application mechanism 197 may be used to apply a specific pressure to a membrane placed between the upper portion 105 and lower portion 150. Pressure may be adjusted by turning the set screw 196.

FIG. 5 is an illustration of a cross-sectional view of one embodiment of the molecular filtration device including a frit. As shown in FIG. 5, when the upper portion 105 and lower portion 150 are fitted together and engaged, a membrane 198 and frit 199 may be compressed between the upper portion 105 and lower portion 150. In one embodiment, the molecular filtration device 100 may be assembled as by placing the frit 199 on the frit supporting lip 159 of the lower portion 150. On top of the frit 199, the membrane 198 of a desired permeability may be placed. Then, on top of the membrane 198, the upper portion 105 may be placed, such that the channel forming lip 110, 111 engages the membrane 198. The frit 199 preferably may have a permeability higher than that of the membrane 198. As shown in FIG. 5, the channel 120 may be a cavity enclosed by the upper portion 105, channel forming lip 110, 111, and membrane 198, wherein the membrane 198 may be structurally supported by the frit 199.

Figure 6:
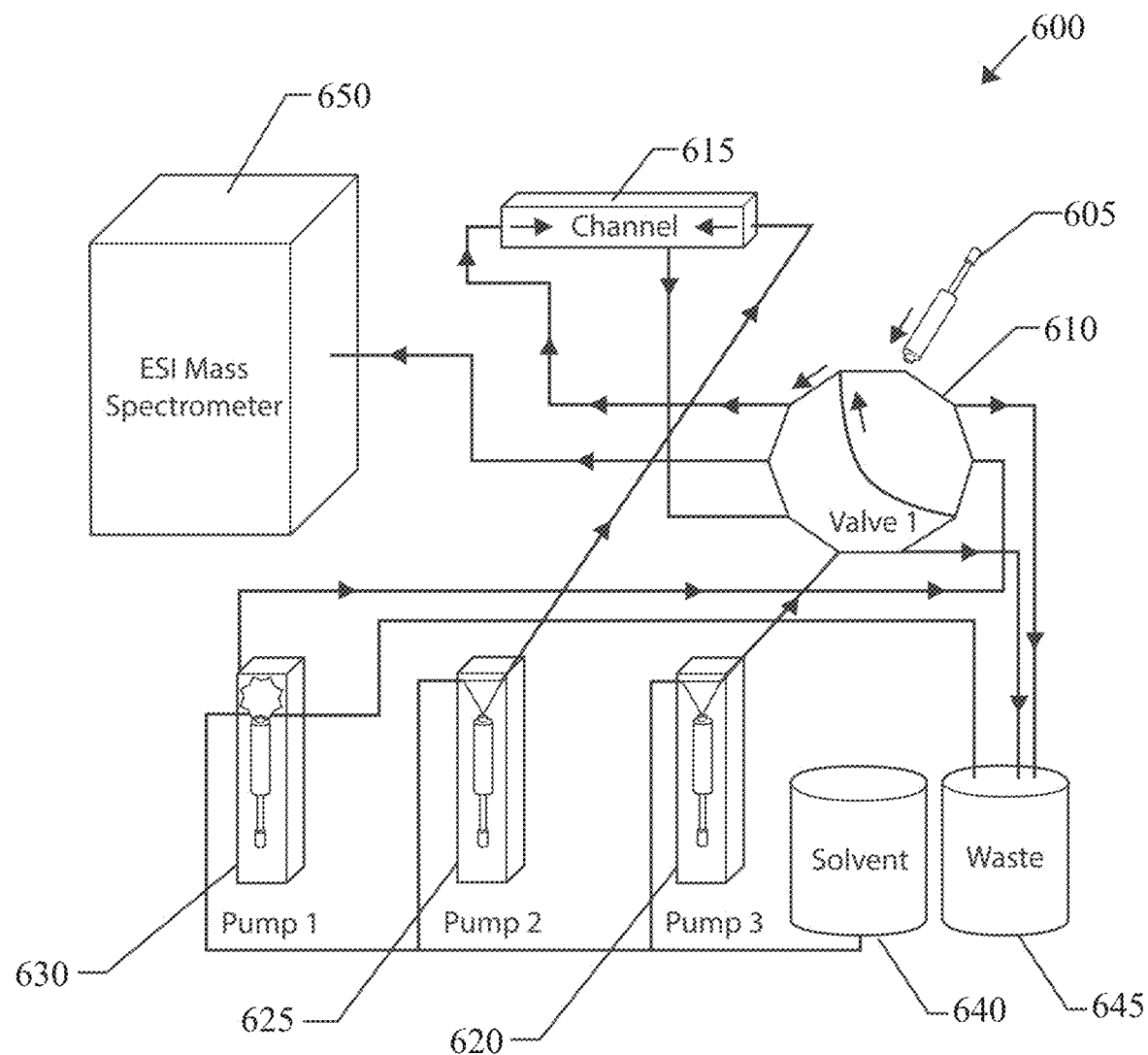
FIG. 6 is a diagram showing the molecular filtration device being prepared for use.

FIG. 6 is a diagram showing the molecular filtration device being prepared for use. As shown in FIG. 6, one embodiment of the molecular filtration system 600 may comprise an injection mechanism 605, injection valve 610, molecular filtration device 615, first pump 630, second pump 625, third pump 620, solvent container 640, waste container 645, and analysis machine 650.

In one embodiment the injection mechanism 605 may be a syringe and during a cleaning protocol, may be used to run a clean buffer solution through the injection valve 610. The pumps 620, 625, 630 may be configured to clean the entire system by flushing clean buffer solution through the flow lines, molecular filtration device 615, and into the waste container 645. After clean buffer is flushed through the flow lines, the sample may be introduced to the system. Specifically, a sample comprising a molecule for filtration and purification may be loaded into the injection mechanism 605 and injected into the injection valve 610. The first pump 630 may then pump the sample into the molecular filtration device 615 via a first upper port. At approximately the same time, the second pump 625 may pump a buffer solution from the solvent container 640 into the molecular filtration device 615 via a second upper port, and the resulting waste solution may be pumped into the analysis machine 650. Once the sample is completely loaded and washed such that impurities able to pass through a membrane of the molecular filtration device 615 are substantially or entirely removed, then what may remain in the molecular filtration device 615, specifically in the channel, may be a sufficiently pure sample.

Figure 7:
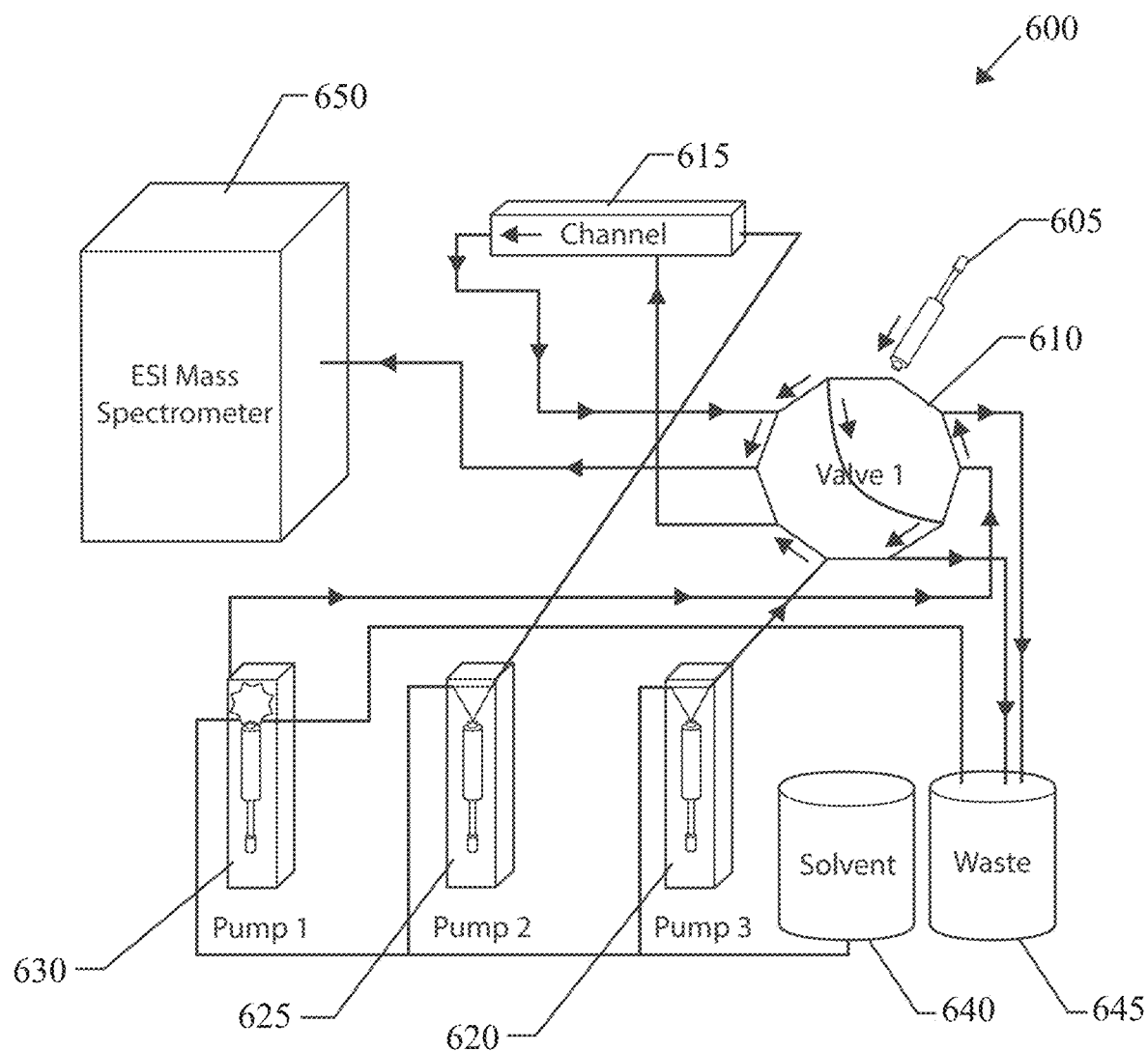
FIG. 7 is a diagram showing the molecular filtration device in use for elution and analysis.

FIG. 7 is a diagram showing the molecular filtration device in use for elution and analysis. After the molecular filtration device 615 contains a sufficiently pure sample, the direction of flow of the pumps 620, 625, 630 may be modified in order to efficiently elute the sample in a high concentration in order to allow for further analysis. Specifically, the second pump 625 may stop pumping, thereby effectively blocking the second port of the molecular filtration device 615. Solution may then be pumped into the lower port of the molecular filtration device 615, and then out of the first upper port and into the injection valve 610. The injection valve 610 may then be configured to directly pump the now purified sample into an analysis machine 650 for further analysis. The entire process shown in FIGS. 6 and 7 may be automated for ease of use and consistency. The analysis machine 650 may be any machine into which a sufficiently pure sample may be analyzed, such as a Mass Spectrometer.

In one embodiment more than one molecular filtration device 615 may be used in parallel. When more than one molecular filtration device 615 is used, the sample may be loaded in approximately 21 seconds, focused/washed in approximately 38 seconds, and eluted in approximately 33 seconds. Additionally, a sample may be loaded/focused on a first molecular filtration device while a sample in a second molecular filtration device is being eluted. In alternate embodiments, the molecular filtration device may proceed with being loaded while a sample is being eluted, in order to increase the throughput of sample in the molecular filtration device. In yet further embodiments, additional molecular filtration devices 615 may be used, provided that hardware is adequate to support said additional molecular filtration devices 615.

Figure 8A:
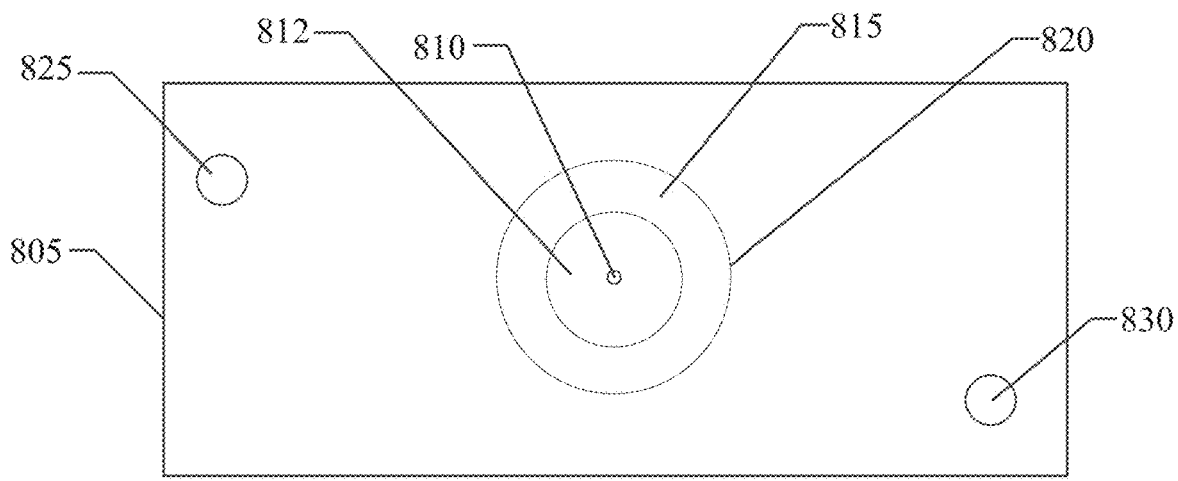
FIGS. 8A-C are illustrations of different channel shapes of the molecular filtration device.
Figure 8B:
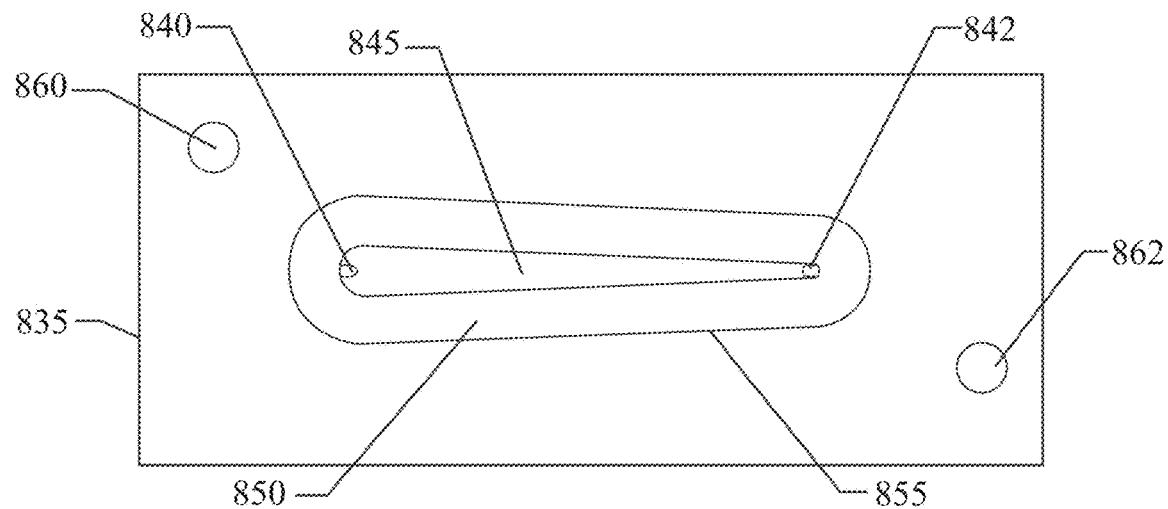
Figure 8C:
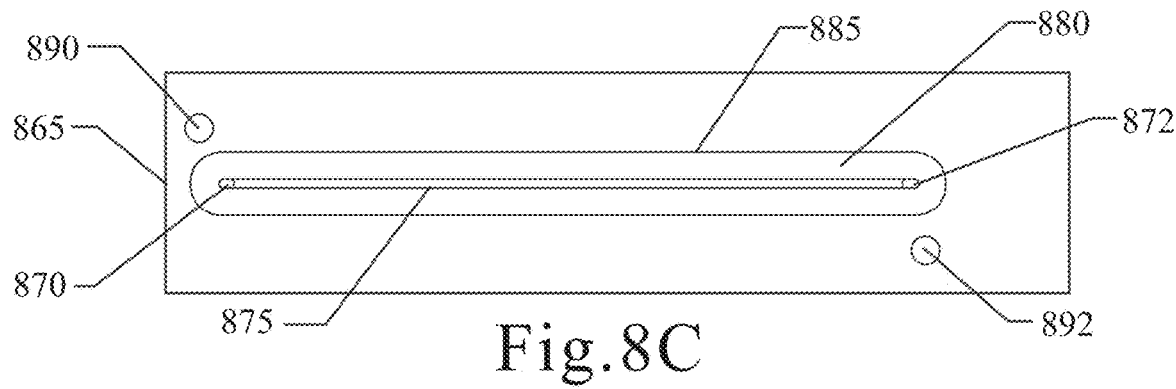

FIGS. 8A-C are illustrations of different channel shapes of the molecular filtration device.

As shown in FIG. 8A, an upper portion 805 may comprise a channel forming cavity 812 that is substantially circular in shape. In this embodiment, the upper portion 805 may have a single upper port 810. The shape of the channel forming cavity 812 may be substantially defined by the channel forming lip 820 and its lower sealing surface 815. The upper portion 805 may also comprise securing structures 825, 830.

As shown in FIG. 8B, an upper portion 835 may comprise a channel forming cavity 845 that is substantially elongated teardrop in shape. In this embodiment, the upper portion 835 may have two upper ports 840, 842. The shape of the channel forming cavity 845 may be substantially defined by the channel forming lip 855 and its lower sealing surface 850. The upper portion 835 may also comprise securing structures 860, 862.

As shown in FIG. 8C, an 865 may comprise a channel forming cavity 875 that may be a substantially elongated oval shape. In this embodiment, the upper portion 865 may have a two upper ports port 870, 872. The shape of the channel forming cavity 875 may be substantially defined by the channel forming lip 885 and its lower sealing surface 880. The upper portion 865 may also comprise securing structures 890, 892.

Figure 9:
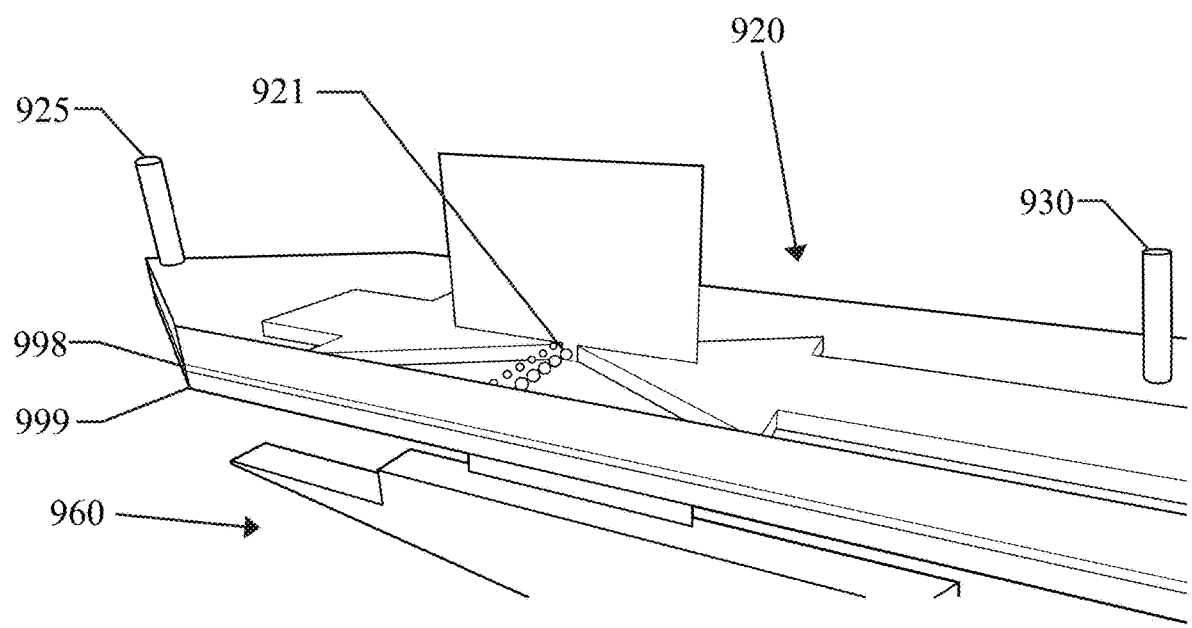
FIG. 9 is an illustration showing a channel of the molecular filtration device.

FIG. 9 is an illustration showing a channel of the molecular filtration device. As shown in FIG. 9, the channel 920 may have solution pumped into it via a first upper port 925 and second upper port 930, which may cause molecules to create a band 921 near a substantial midpoint of the flow caused by the first upper port 925 and second upper port 930. The flow of solution may then cause molecules, including solvent, smaller than a particular size to cross a membrane 998 and frit 999 and pass into the reservoir 960 or outflow mechanism. The creation of the band 921 allows for the membrane 998 to remain relatively unclogged, and allow for greater filtration, washing, and concentration of molecules caught in the band 921.

Experiment 1: Pressure Test on Compressed Membrane

Figure 10:
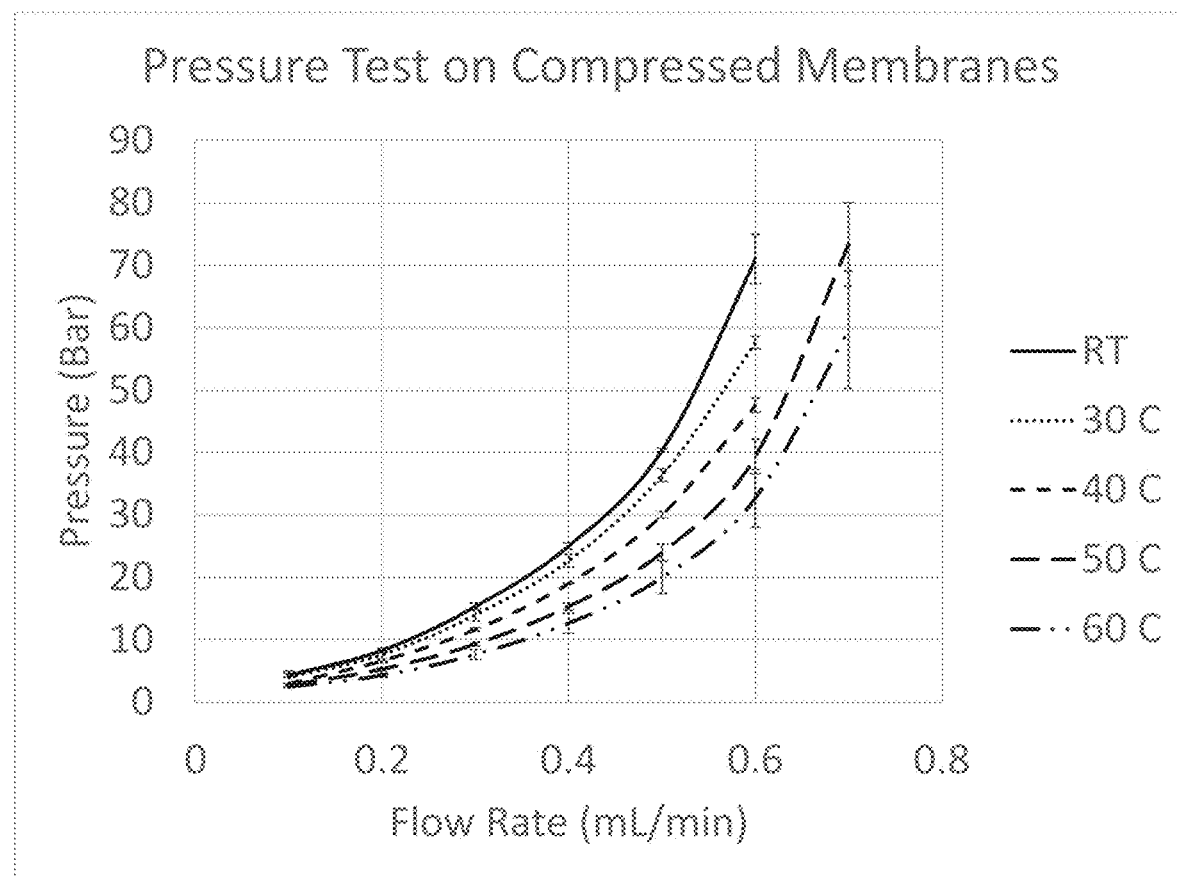
FIG. 10 is a graph showing flow rate v. pressure for compressed membranes in the molecular filtration device.

The effects of pressure on a membrane compressed by the device of the present disclosure was tested. A 10 kDa membrane was installed in a molecular filtration device, and the flow rate was increased until the pressure on the membrane by the flow of solution reached 100 bar. The results of this experiment are shown in FIG. 10. Importantly, it was discovered that the membrane being compressed by the molecular filtration device of the present disclosure must be pressurized up to 100 bar in order to allow for the pressure measurements to increase as observed by increasing flow rate. One potential explanation for this is that the spun support on which the membrane is cast may have been crushed, leading to increased back pressure.

Experiment 2: Behavior of Unpressurized Membrane

Figure 11:
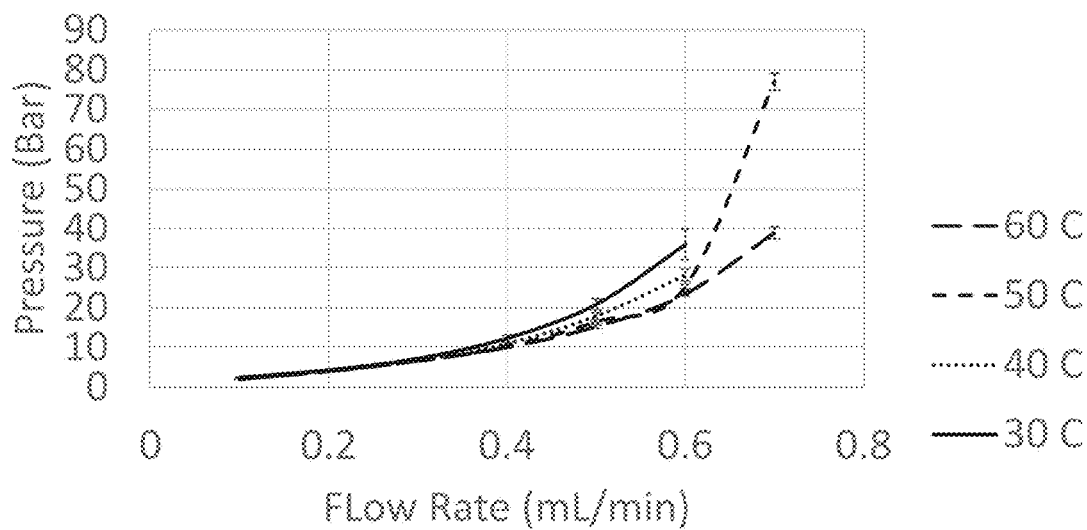
FIG. 11 is a graph showing flow rate v. pressure for uncompressed membranes in the molecular filtration device.

The effects of pressure on an uncompressed membrane was tested. A 10 kDa membrane was installed in a molecular filtration device, and flow rate was increased. The results of this experiment are shown in FIG. 11. Importantly, it was discovered that the pressure experienced by the uncompressed membrane, compared to the compressed membrane of Experiment 1 hereinabove, was significantly less than when the membrane was compressed. Additionally, when the membrane was uncompressed, the temperature of the experiment had a significantly smaller effect on the relationship between flow rate and pressure. The data shows that a useful forward flow rate may be around 500 uL/min.

Experiment 3: Reverse Flow Through Membrane

Figure 12:
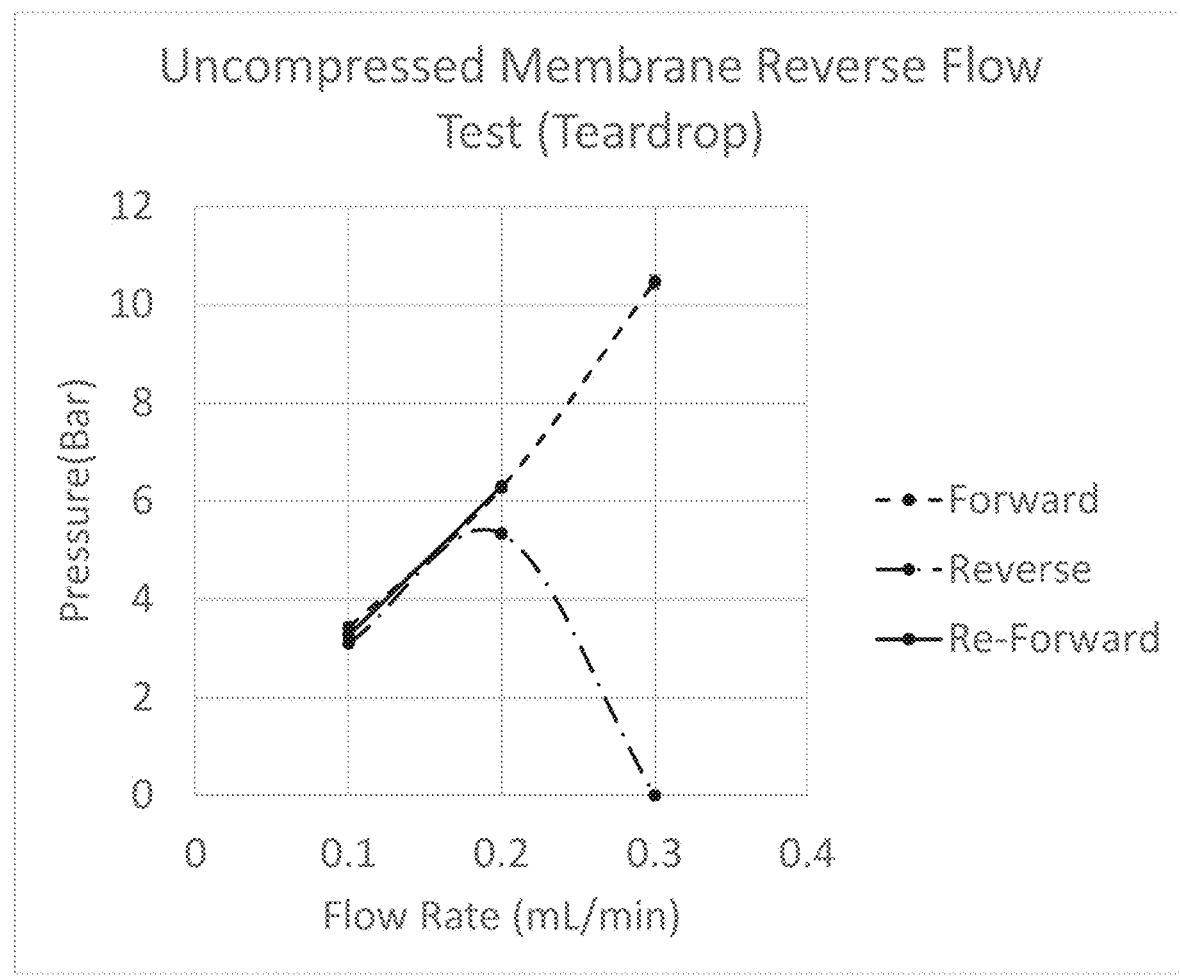
FIG. 12 is a graph showing flow rate v. pressure for different flow directions in the molecular filtration device.

The effects of reversing flow of solution at different flow rates was measured. A 10 kDa membrane was installed in a molecular filtration device, and the flow was forward, reversed, and then re-forwarded at increasing flow rates. The results of this experiment are shown in FIG. 12. The membrane experienced failure when in a reverse flow rate of between 200 and 300 uL/min were applied. Thus, a useful reverse flow rate was between 100 and 200 uL/min, which may be somewhat comparable to current 2.1 mm column chromatographic methods.

Experiment 4: Forward Flow Through Uncompressed 1 kDa Membrane

Figure 13:
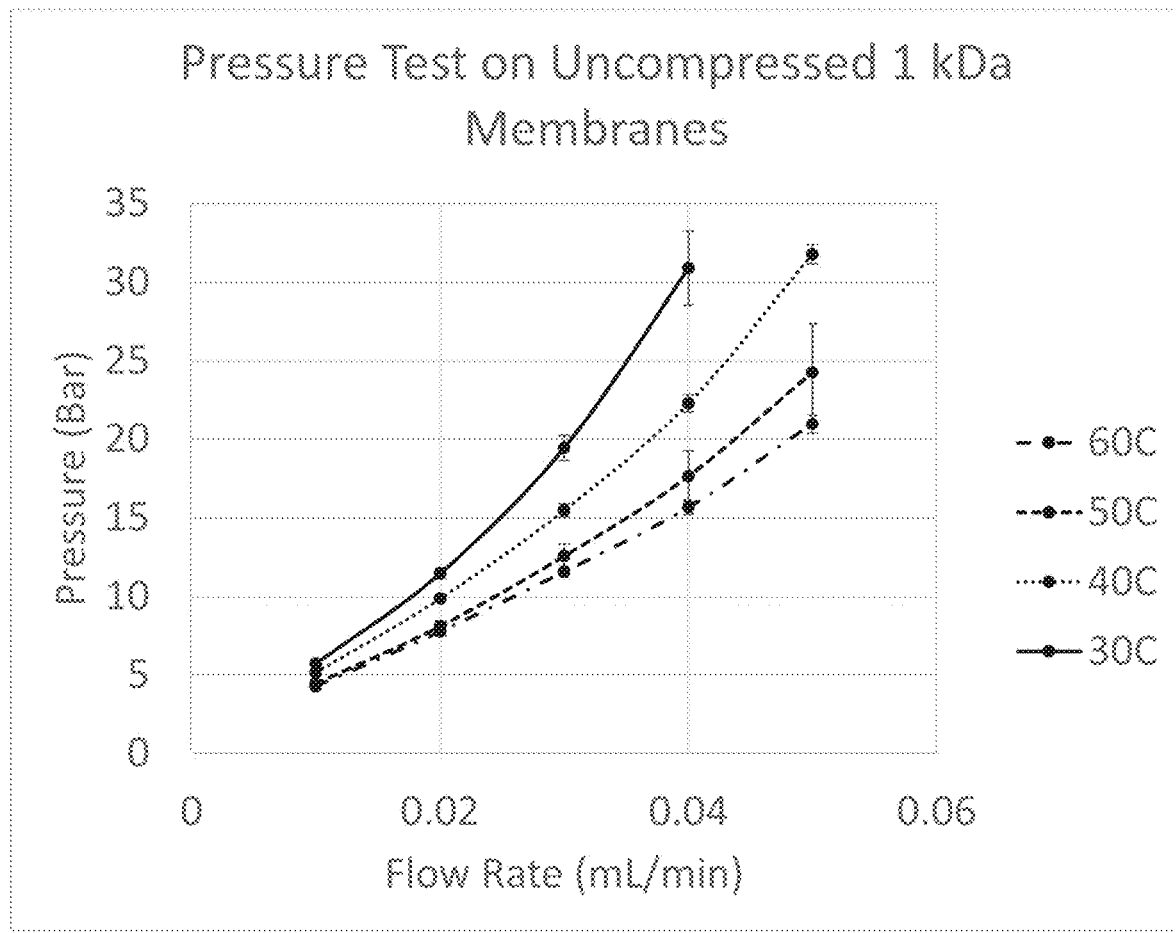
FIG. 13 is a graph showing flow rate v. pressure for uncompressed 1 kDa membranes in the molecular filtration device.

The effects of pressure on an uncompressed membrane was tested. A 1 kDa membrane was installed in a molecular filtration device, and flow rate was increased. The results of this experiment are shown in FIG. 13. The 1 kDa membrane experienced pressures approximately 10× that experienced by a 10 kDa membrane at similar flow rates. Experiments with 1 kDa membranes and 10 kDa membranes experienced similar pressures when the flow rate of the 10 kDa membrane was 10 times that of the 1 kDa membrane.

Experiment 5: Reverse Flow Through 1 kDa Membrane

Figure 14:
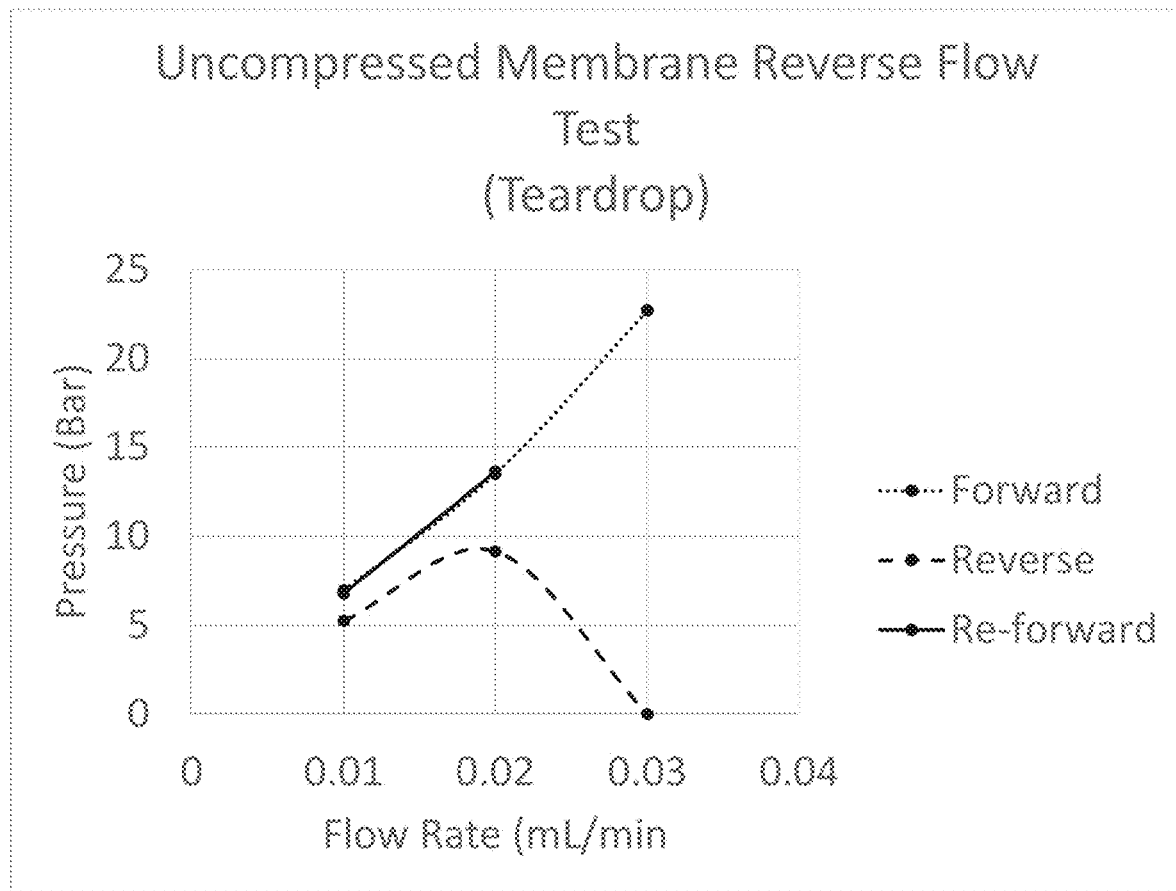
FIG. 14 is a graph showing flow rate v. pressure for different flow directions in the molecular filtration device with a 1 kDa membrane.

The effects of reversing flow of solution at different flow rates was measured. A 1 kDa membrane was installed in a molecular filtration device, and the flow was forward, reversed, and then re-forwarded at increasing flow rates. The results of this experiment are shown in FIG. 14. The membrane experienced failure when in a reverse flow rate of between 20 and 30 uL/min were applied. Thus, a useful flow rate, forward and backward, was between 10 and 20 uL/min. Similar to Experiment 3, the data indicates that the membrane becomes ruptured around 10 bar.

Experiment 6: Reverse Flow Analysis of Various Channel Geometries

Figure 15:
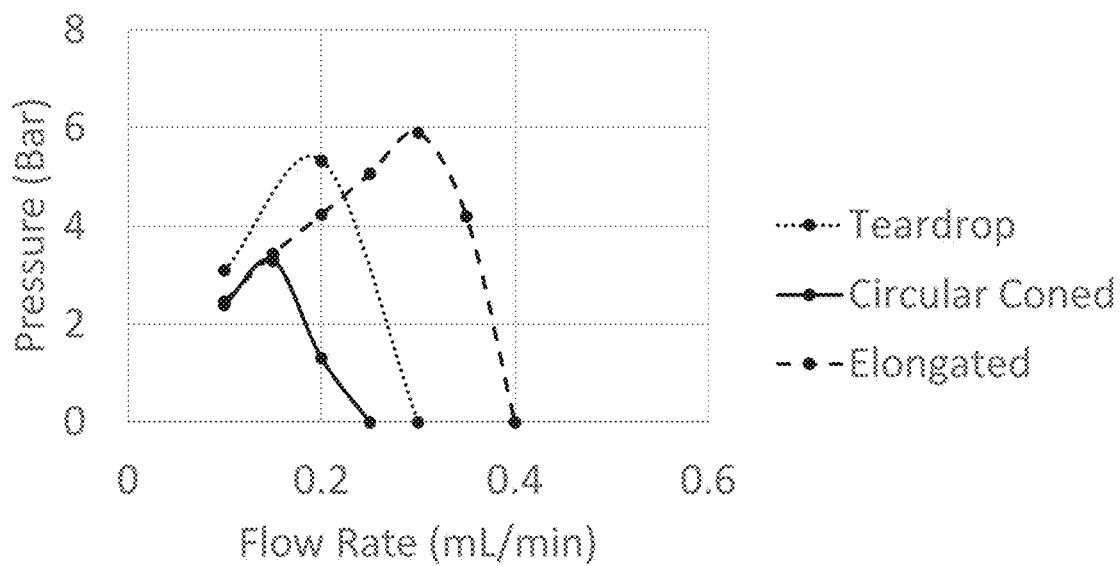
FIG. 15 is a graph showing the effects of channel geometry on membrane stability.

The effects of channel shape and its effects on membrane stability at different flow rates was measured. The results of this experiment are shown in FIG. 15. As shown in FIG. 15, the shape of the channel has a significant effect on the amount of pressure the membrane may be able to tolerate when flow is reversed before experiencing structural failure. Particularly, the elongated shaped channel is the most resilient, while the circular coned shaped channel is the least resilient of the three channel shapes tested. The teardrop shaped channel's resilience is between that of the elongated shape and circular cone shaped channels. The elongated channel has a 0.03 mm maximum span, and a 150 um channel height. The teardrop channel has a 0.125 mm maximum span and a 250 um channel height. The circular channel has a 0.343 mm maximum span, and a coned height of 250 um to 450 um or flat 150 um channel height.

An increased span generally results in a lower reverse membrane flow rate due to membrane lift resulting from no frit or supporting structure above the membrane.

Experiment 7: Comparison of Molecular Filtration Device and Standard Chromatography A comparison of the molecular filtration device and standard chromatography was conducted. Both the molecular filtration device and chromatography were analyzed by a Q Exactive™ Plus mass spectrometer, manufactured by Thermo Scientific™.

The chromatography included: 2.1 mm i.d. Agilent PLRP-S column; at 65 C; sample injection volume of 5 µL having 100 ng of sample; flow rate of 100 µL/min; A: 0.1% FA B: ACN+0.1% FA; and Gradient: 0 min 20% b; 2 min 20%; 4.75 min 65%; 5 min 80% b; 5.5 min 15%; 5.75 85%; 6 min 15%; 6.25 85%; 6.5 min 15% 1605.

The molecular filtration device had a flow rate of 100 uL/min, with a 100 uL sample injection volume having 100 ng of sample 1600.

Figure 16:
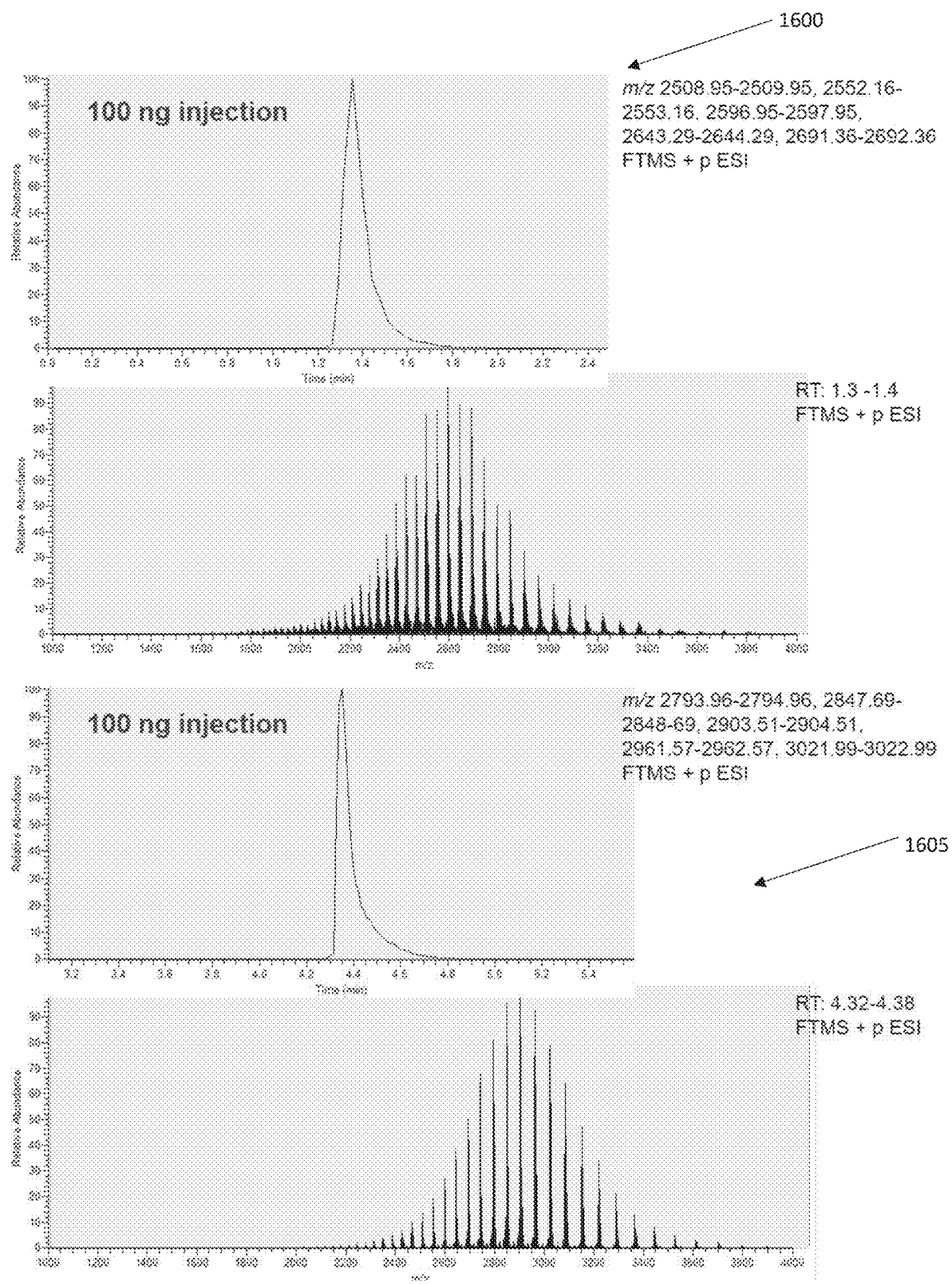
FIG. 16 is a set of graphs showing the efficacy of the molecular filtration device compared to traditional filtration methods.

As shown in FIG. 16, despite the fact that the chromatography method included a much smaller sample injection volume, the molecular filtration volume eluted the desired sample with in a band similar to that of chromatography. Further, the molecular filtration device was able to elute the sample much more quickly than the chromatography method. Accordingly, the molecular filtration device is highly effective at analyzing significantly more dilute samples than traditional methods, including liquid chromatography.

Experiment 8: Molecular Filtration Device to Mass Spectrometer

Figure 17:
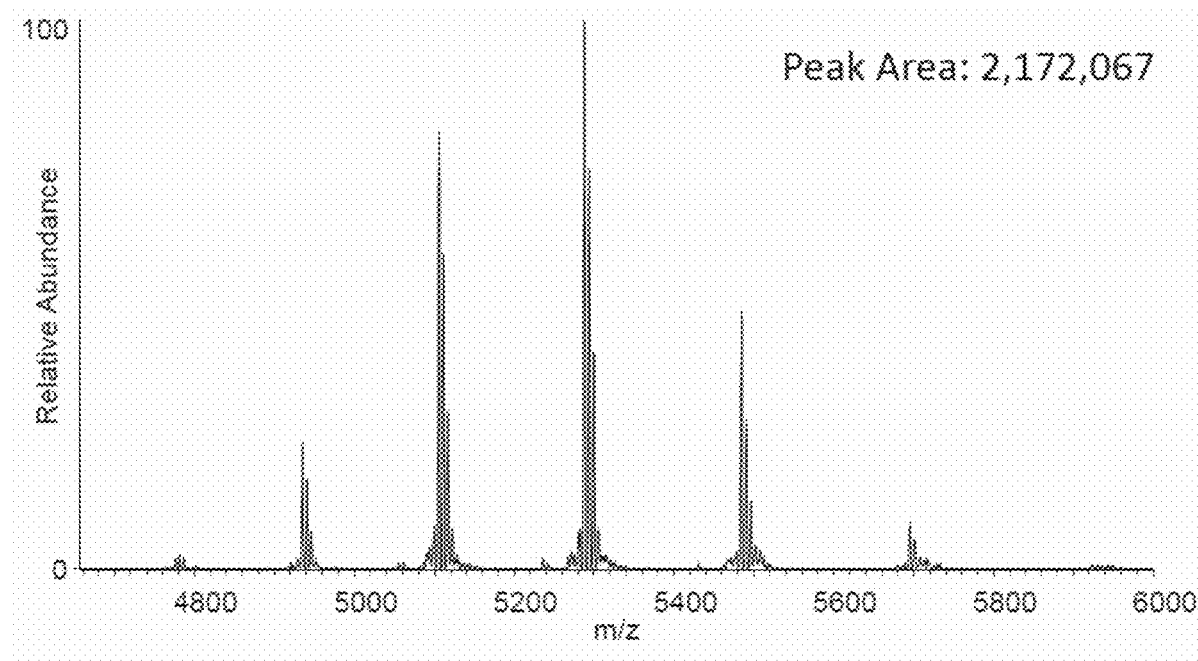
FIG. 17 is a graph showing data related to a sample processed by the molecular filtration device and transferred directly to a mass spectrometer, wherein the sample is 500 ng.
Figure 18:
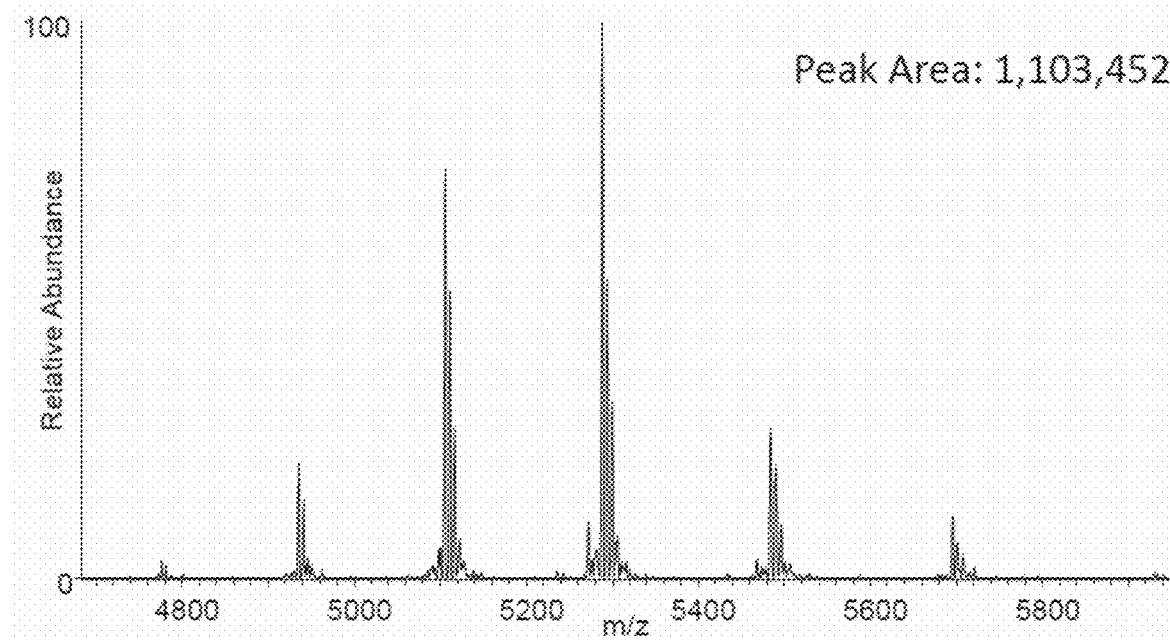
FIG. 18 is a graph showing data related to a sample processed by the molecular filtration device and transferred directly to a mass spectrometer, wherein the sample is 250 ng.

A sample of Herceptin in excipient was loaded onto a molecular filtration device and analyzed by a Q Exactive™ Plus mass spectrometer. A volume of 5 uL containing 250 ng or 500 ng of sample was loaded onto the molecular filtration device, was washed for 30 seconds with 300 uL, and eluted with 55 uL at a rate of 100 uL/min. The sample was eluted directly onto a mass spectrometer with 30 a.u. sheath; 10 a.u. aux; 300 C HESI probe; 275 C ion transfer tube; 100 V SID; 10 V HCD; Pressure reg setting: 4; 5 uscans; and 17,500 res @ m/z 200. The result of loading 500 ng is shown in FIG. 17 and the result of loading 250 ng is shown in FIG. 18.

The ratio of the peaks loaded is 0.508, which indicates a quantitative response and provided superior data to traditional methods of analysis. Further, the nature of the loading and washing of sample on the molecular filtration device allows for the ability for the user to change between denatured and native forms from run to run by specifying a different solvent, wherein up to five (5) different solvents may be connected to the system at any given time.

Experiment 9: Reverse Flow Elution v. Cross Flow Elution

Figure 19:
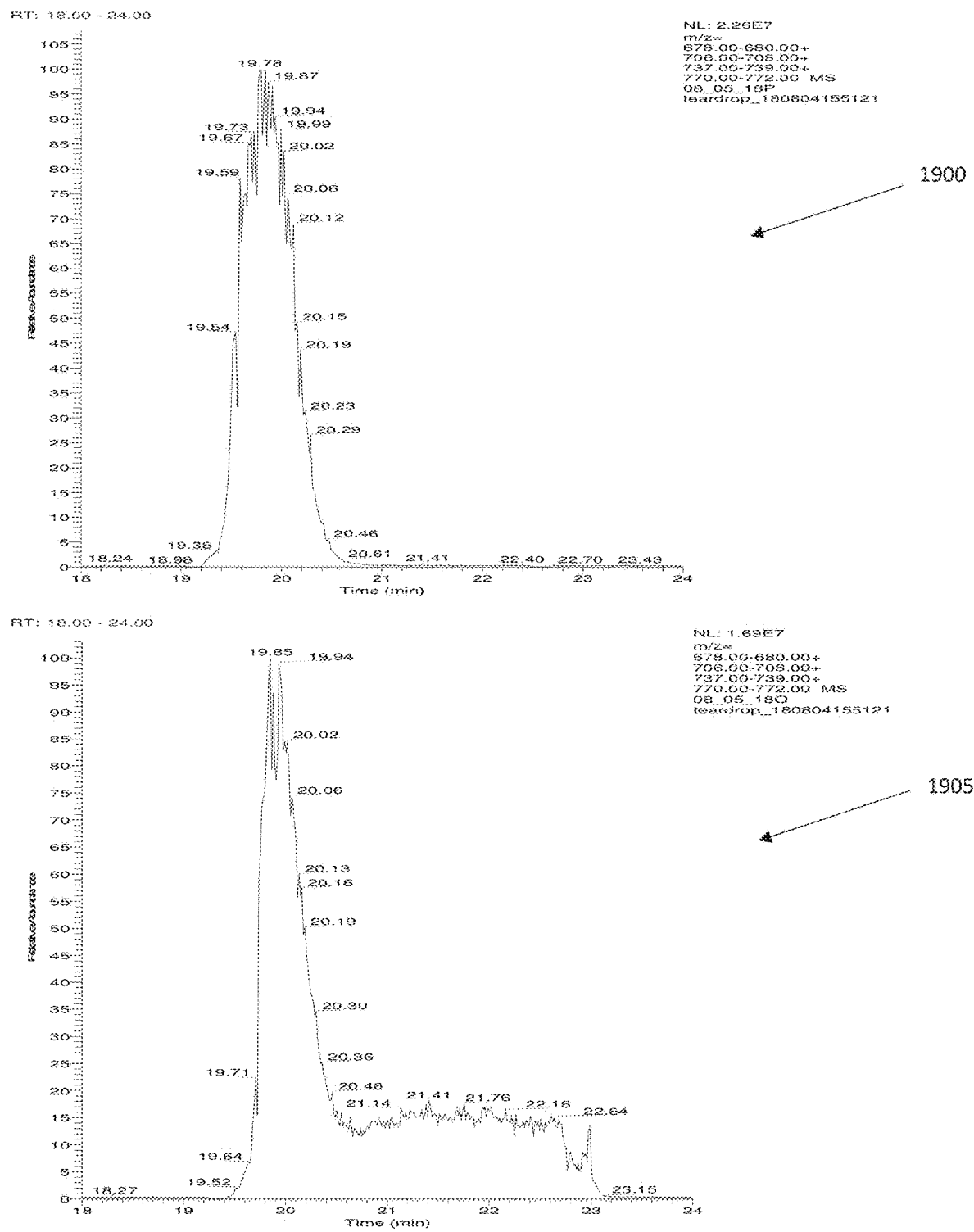
FIG. 19 is a set of graphs showing the increased efficacy of reverse flow elution as compared to cross flow elution.

A comparison was made between elution completed by reverse flow elution and cross flow elution while utilizing the molecular filtration device. The result of this elution comparison is shown in FIG. 19. As shown in FIG. 19, reverse flow elution creates a single sharp peak 1900, and cross flow elution creates a sharp peak followed by a tail end 1905. Both methods were performed using the same samples, solutions, pressures, and other conditions, and the only difference was the elution method. Specifically, reverse flow elution is conducted by preventing flow through a first upper port of the molecular filtration device and reversing flow of solution through a lower port of the molecular filtration device such that the sample is eluted out of the channel via the second upper port. The cross flow elution means that flow is prevented from passing through the lower port of the molecular filtration device, such that the sample is eluted through the second upper port.

Figure 20:
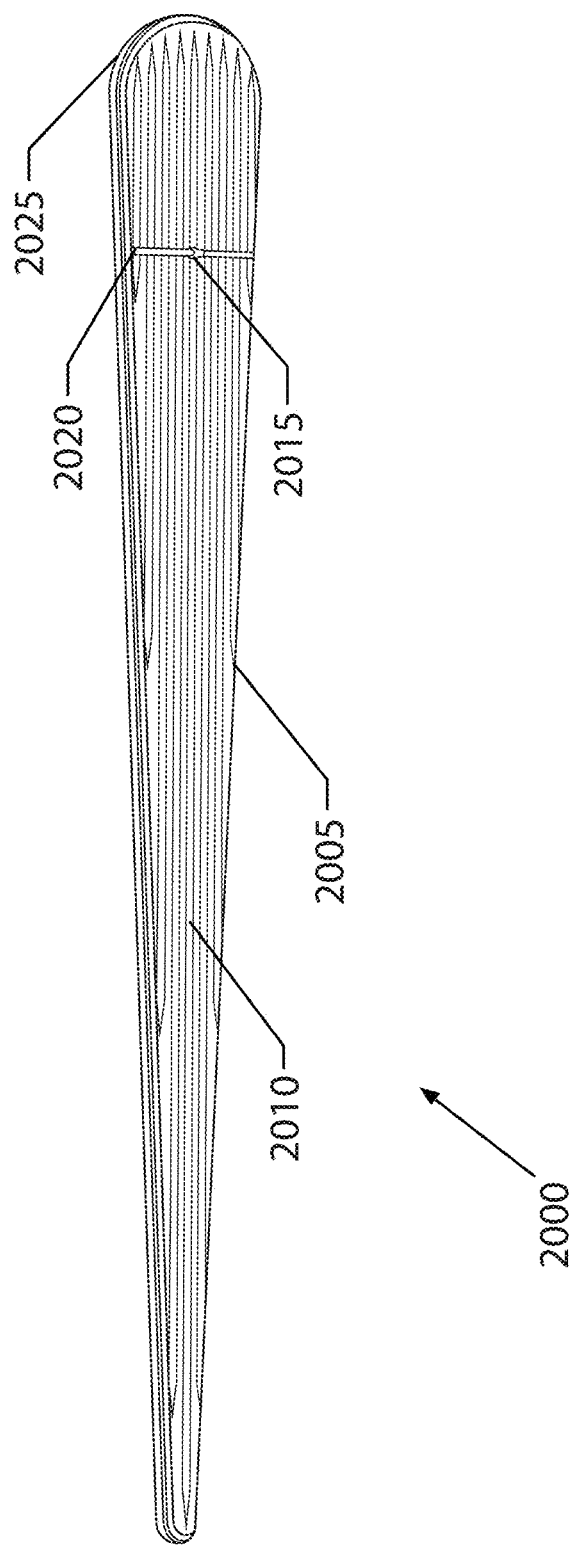
FIG. 20 is an illustration showing one embodiment of a grooved frit.

FIG. 20 is an illustration showing one embodiment of a grooved frit. As shown in FIG. 20, the grooved frit 2000 may comprise a main body 2005, a plurality of grooves 2010, a drain hole 2015, a transverse crossing lane 2020, and a perimeter lip 2025. The plurality of grooves 2010 may be parallel or substantially parallel and longitudinally traverse the main body 2005. The plurality of grooves 2010 may be varying lengths in order to substantially cover the surface of the main body 2005, despite contours in the shape of the main body 2005.

The drain hole 2015 may be located substantially anywhere on the main body 2005, but is preferably located on the transverse crossing lane 2020. In one embodiment, the drain hole 2015 may be at a center of said transverse crossing lane 2020. In one embodiment, the transverse crossing lane 2020 is substantially perpendicular to the plurality of grooves 2010.

As shown in FIG. 20, the main body 2005 may be teardrop shaped. In alternative embodiments, the main body 2005 may be oval, oblong, elongated rectangle shaped, or substantially any shape that may be received by a reservoir, as the term reservoir is used hereinabove.

The frit 2000 may be used to support a mesh, which may in turn support a membrane, as used hereinabove, in a molecular filtration apparatus. The plurality of grooves 2010 may increase directional flow and reduce the effects dead spots of solution flow along the frit 2000 and by extension, the membrane. This may be advantageous because it allows solution to flow relatively uniformly over the membrane and frit 2000, preventing the creation of uneven deposits of molecules on the membrane.

In one embodiment, the frit 2000 may be a substantially non-porous material. In one embodiment, the plurality of grooves 2010 may create drain lanes that are 0.005 inches (") wide and 0.005" deep, wherein the grooves extend outward from a surface of the frit 2000 at a 45 degree angle. The perimeter lip 2025 may be 0.005" wide and 0.005" deep. The transverse crossing lane 2020 may be 0.005" wide and 0.005" deep.

Figure 21:
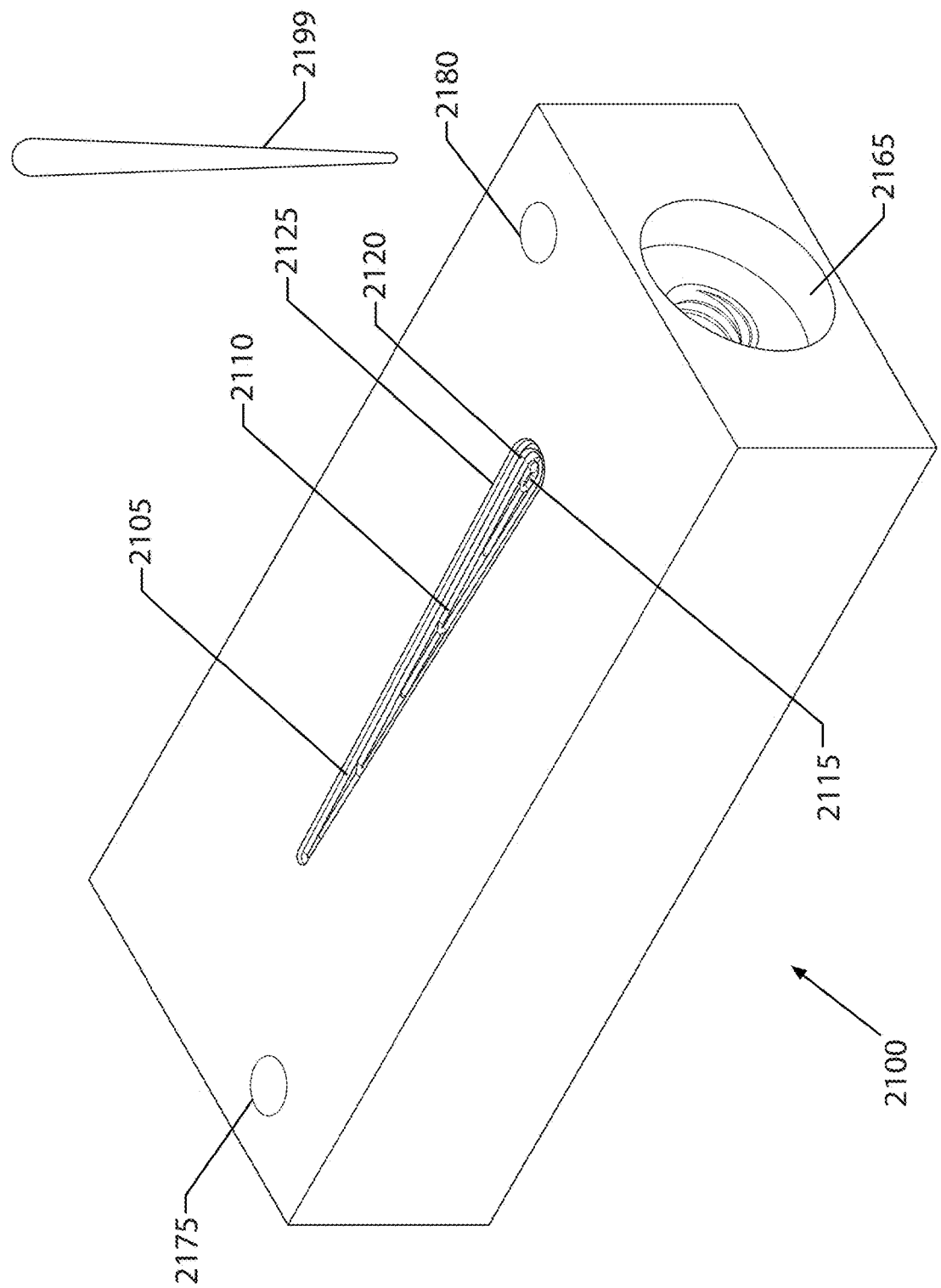
FIG. 21 is an illustration of a perspective view of one embodiment of a lower portion.

FIG. 21 is an illustration of a perspective view of one embodiment of a lower portion. As shown in FIG. 21, the lower portion 2100 may comprise a reservoir 2105, a plurality of grooves 2110, a drain hole 2115, a transverse crossing lane 2120, a perimeter lip 2125, a lower port 2165, and lower securing structures 2175, 2180.

The lower portion 2100 of FIG. 21 may be configured to have a substantially similar use and function as the lower portion 150 shown and described in FIG. 1, hereinabove. In some embodiments, the lower portion 2100 of FIG. 21 may be configured to replace the lower portion 150 of FIG. 1. The lower portion 2100 may be configured to work with or otherwise engage the upper portion 105, as shown and described in FIG. 1.

The plurality of grooves 2110 may be parallel or substantially parallel and longitudinally traverse a base of the reservoir 2105. The plurality of grooves 2110 may be of varying lengths such that the plurality of grooves may be configured to create a plurality of channels that are substantially similar in width and are distributed along the base of the reservoir 2105.

The transverse crossing lane 2120 may be substantially perpendicular to the plurality of grooves 2110, such that the transverse crossing lane 2120 may be configured to allow solution that travels along the channels created by the plurality of grooves 2110 to be consolidated. The transverse crossing lane 2120 may be positioned toward one end of the reservoir 2105. In one embodiment, the drain hole 2115 may be located on the transverse crossing lane 2120. Preferably, the drain hole 2115 may be located at a center portion of the transverse crossing lane 2120. The drain hole 2115 may be in fluid communication with the lower port 2165, such that solution may travel along the channels created by the plurality of grooves 2110, into the transverse crossing lane 2120, and through the drain hole 2115, such that the solution exits the lower portion 2100 through the lower port 2165.

The perimeter lip 2125, may be configured to be an indentation from a top surface of the lower portion 2100. The perimeter lip 2125 may be configured to receive a mesh 2199 or other supporting structure, that may be configured to provide support to a membrane at rest on the top surface of the lower portion 2100. The mesh 2199 is preferably porous and may allow solution to flow through it relatively unobstructed. The mesh 2199, when in at an rest state, is preferably slightly larger in surface area than the perimeter lip 2125, such that the mesh 2199 may be flexed in order to engage the perimeter lip 2125. In this flexed state, the mesh 2199 may form a snug seal against the perimeter lip 2125, and provide support for the membrane. The mesh 2199 may be a laser cut 165×800 (0.0065" thick, 25 μm pore size) twill Dutch weave 316SS wire mesh.

The plurality of grooves 2110 may be used to support the mesh 2199, which may in turn support a membrane, as used hereinabove, in a molecular filtration apparatus. The plurality of grooves 2110 reduces the amount of dead space by directing flow of solution in the reservoir 2105 and by extension, the membrane. This may be advantageous because it allows solution to flow relatively uniformly over the membrane, preventing the creation of uneven deposits of molecules on the membrane.

In one embodiment, the plurality of grooves 2110 may have a height that is equal to or slightly less than the height of the reservoir 2105. In some embodiments, the plurality of grooves 2110 may have a height such that the top of the plurality of grooves 2110 may be in line with the perimeter lip 2125.

Figure 22:
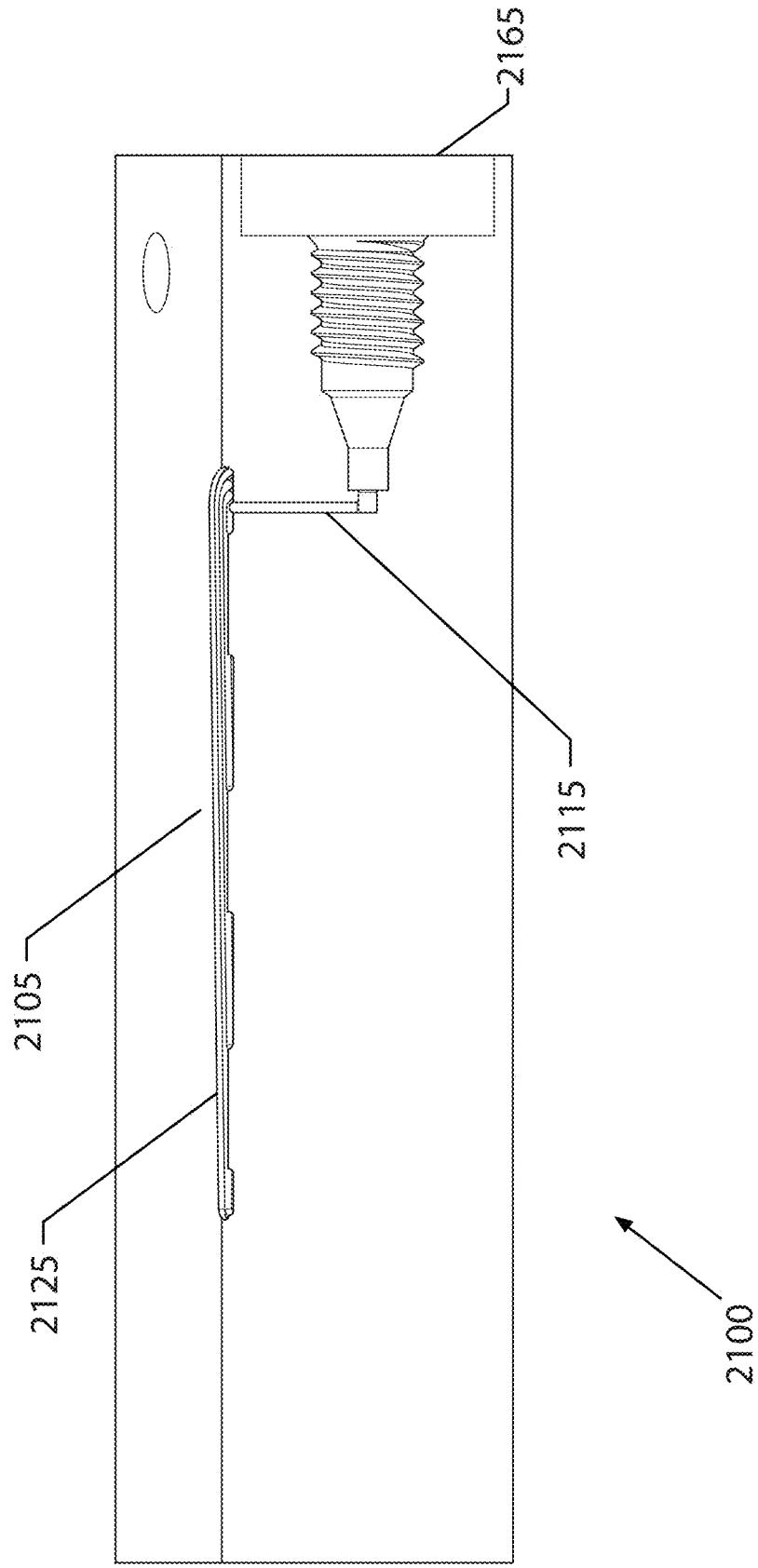
FIG. 22 is an illustration of a transparent side view of one embodiment of a lower portion of the molecular filtration device.

FIG. 22 is an illustration of a transparent side view of one embodiment of a lower portion of the molecular filtration device. As shown in FIG. 22, the lower portion 2100 may comprise a lower port 2165, perimeter lip 2125, drain port 2116, which may be connected to drain hole 2115, and reservoir 2105. The lower end of lower port 2165 may be configured to receive a lower flow device. The perimeter lip 2125 may be configured to receive the mesh 2199.

Figure 23:
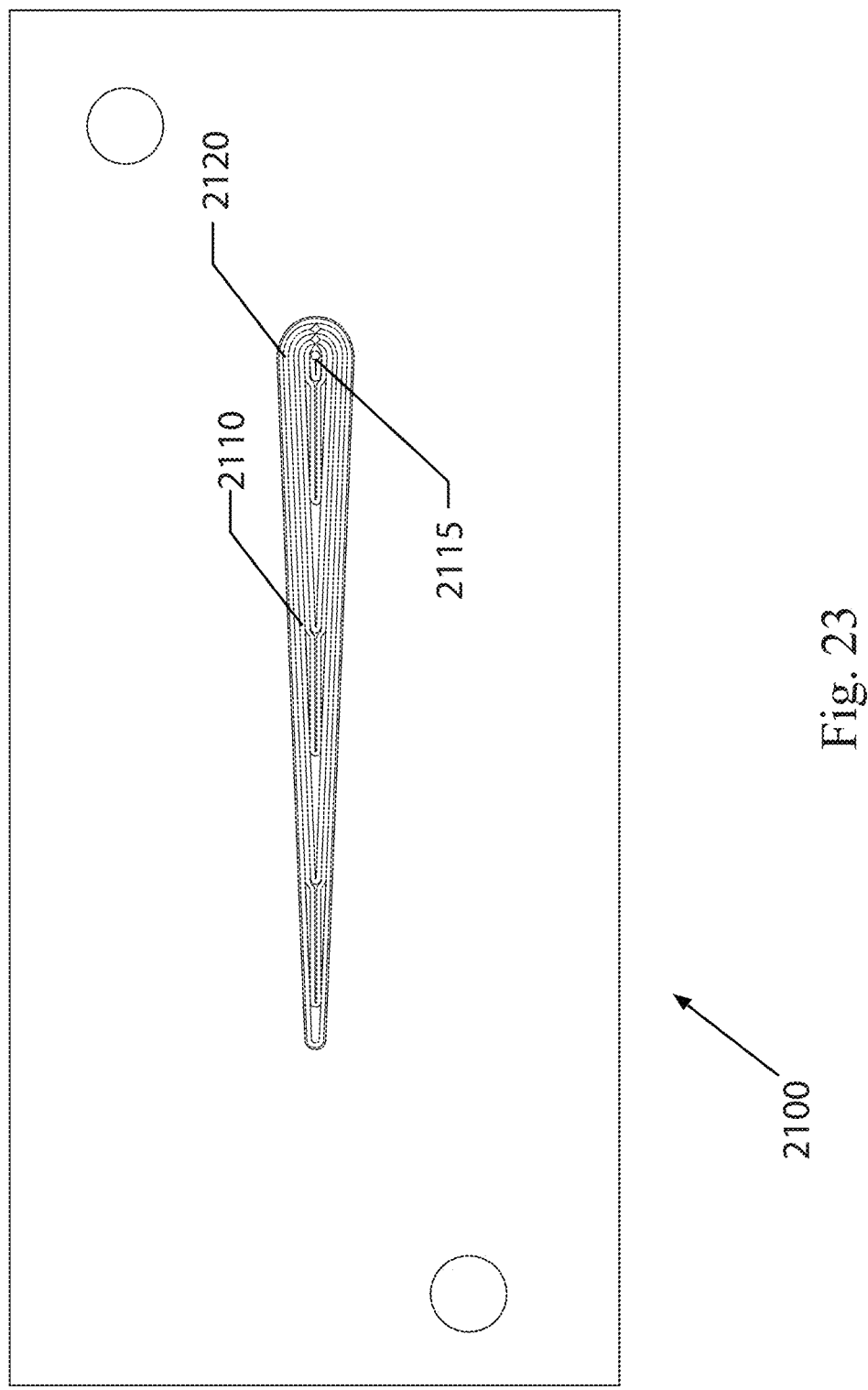
FIG. 23 is an illustration of a top view of the lower portion showing the plurality of grooves.

FIG. 23 is an illustration of a top view of the lower portion showing the plurality of grooves. As shown in FIG. 23, the lower portion 2100 may comprise the plurality of grooves 2110 arranged in such a configuration to match a channel forming cavity, such as the channel forming cavity 845 shown and described in FIG. 8B.

Figure 24:
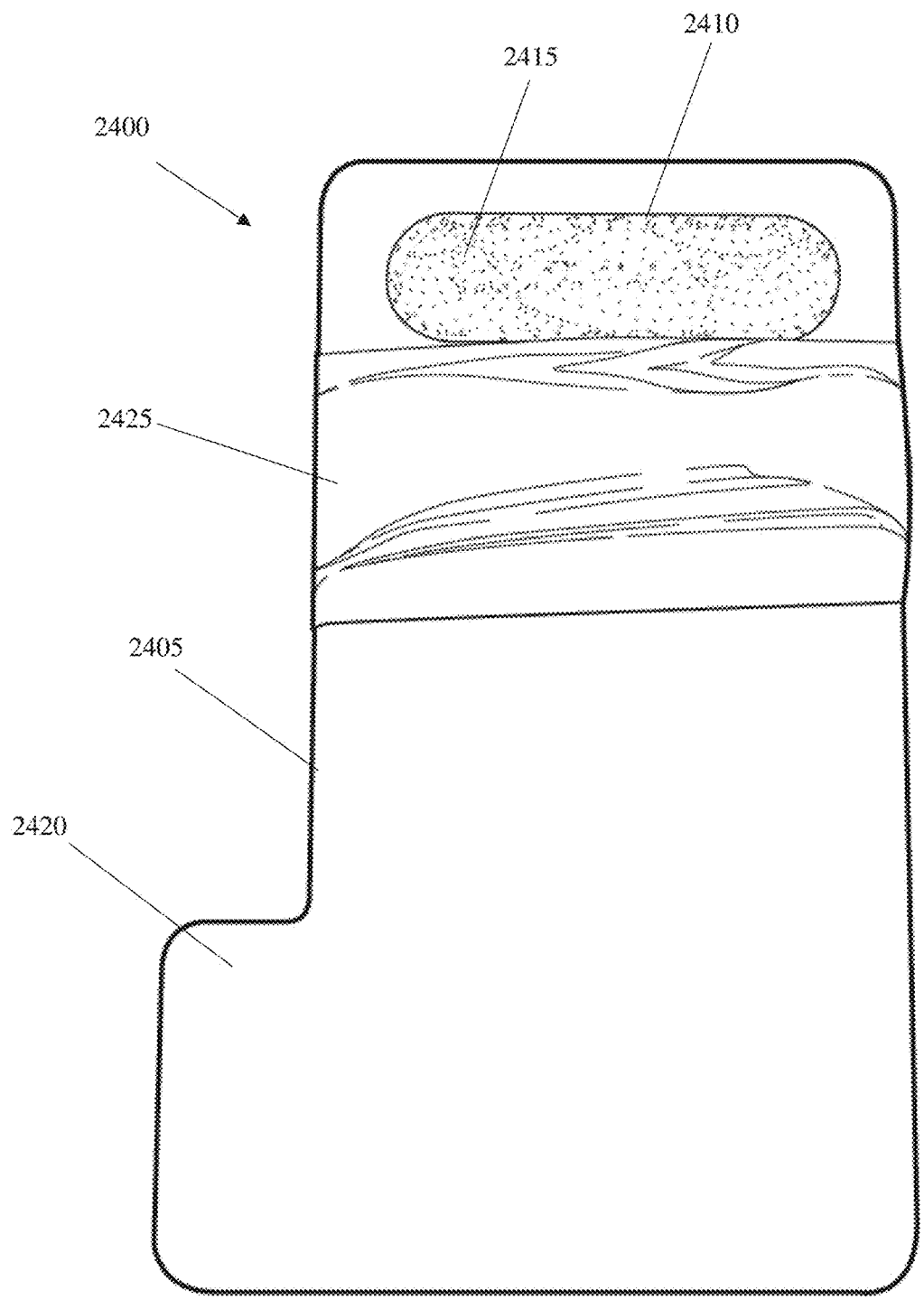
FIG. 24 is an illustration of one embodiment of a consumable device for use with a molecular filtration device.

FIG. 24 is an illustration of one embodiment of a consumable device for use with a molecular filtration device. As shown in FIG. 24, the consumable device 2400 may comprise a main body 2405 and membrane 2415.

The main body 2405 may comprise two layers. The main body 2405 may comprise a window 2410 on both layers, and a membrane 2415 may be placed between the two layers such that the membrane 2415 fills the window 2410.

The main body 2405 may comprise a tab 2420. The tab 2420 may be a substantially solid and opaque material configured to block or disrupt the transmission and/or receiving of an optical signal, such as an infrared (IR) beam. In some embodiments, the main body 2405 may be a rigid flat structure. In some embodiments, the main body 2405 may comprise a Delrin® material, having a total thickness of approximately 0.050". In some embodiments, the main body 2405 may be substantially rigid or may be flexible. In some embodiments, the tab 2420 may also function to prevent a user from inserting the consumable device 2400 into the molecular filtration device in an unintended orientation or in an orientation that would cause the molecular filtration device to not function as intended. In some embodiments, the tab 2420 may solely function to be an optical signal blocker. In alternate embodiments, the optical signal may be any type of signal transmissible and detectable over an atmospheric volume. In some embodiments, the tab 2420 may be configured to engage a mechanical switch, such that when the consumable device 2400 is used, the tab 2420 pushes or otherwise comes into contact with a physical object, which may be required in order for the molecular filtration device to function. In some embodiments, the tab 2420 may be configured to trigger a sensor such that physical contact between the tab 2420 and physical structure may not be required in order for the molecular filtration device to function.

Figure 27:
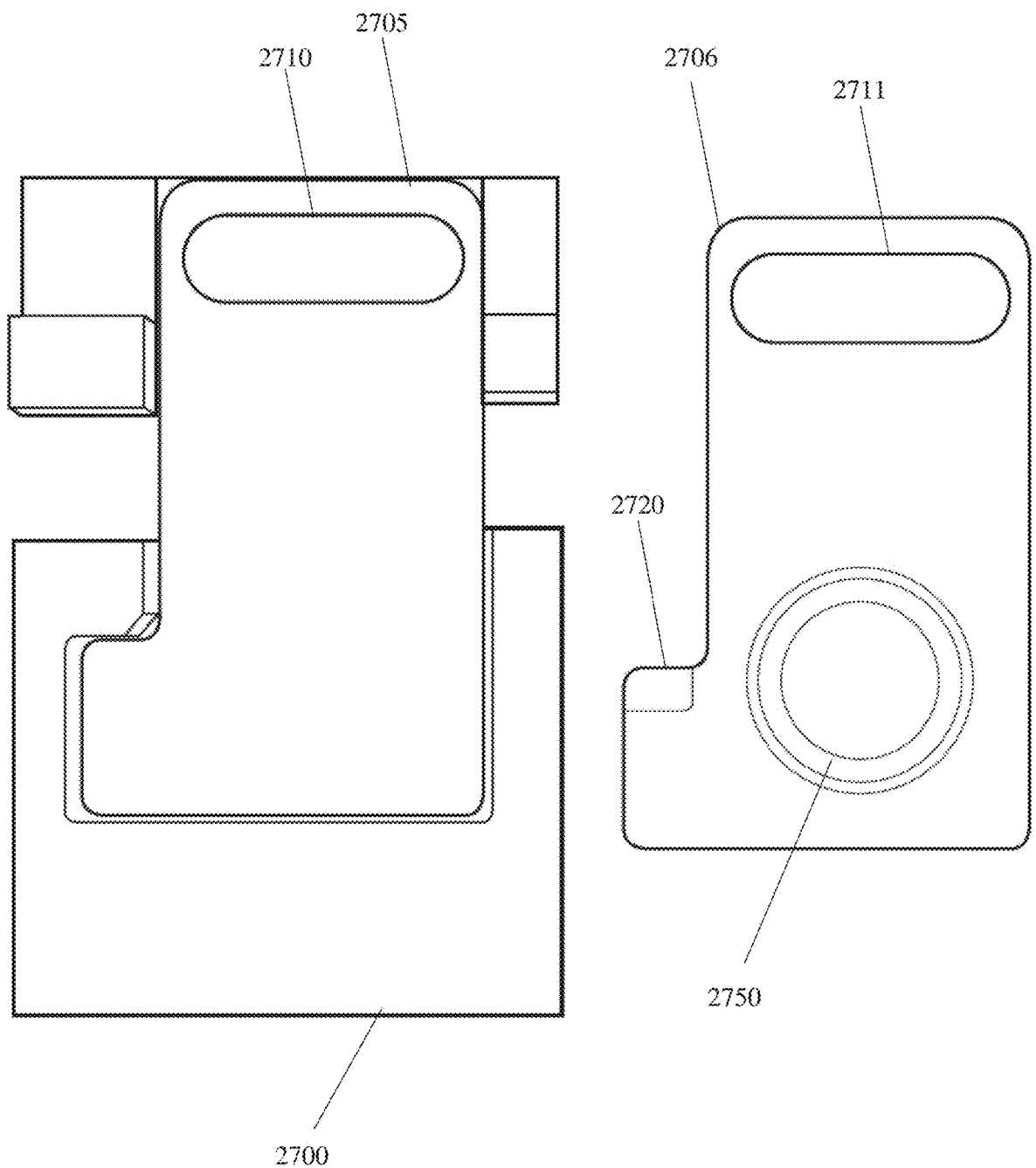
FIG. 27 is an illustration of one embodiment of a stencil that may be used to assemble a consumable device.

Additional components may also be placed between the two layers of the main body 2405. In one embodiment, an electronic tag 2750, as shown in FIG. 27, may be placed between the two layers. The electronic tag 2750 may be an RFID tag. In some embodiments, the electronic tag 2750 may comprise verification data. The verification data may be a series of characters, computer code, or one or more encryption keys configured to be detected and read by the molecular filtration device. In some embodiments, the molecular filtration device may be configured to not change to a closed configuration if a specific, or correct, verification data is not detected or read by the molecular filtration device, as discussed above. In some embodiments, where the main body 2405 is a single layer, additional components may be embedded in the layer, or attached to an exterior surface of the single layer. In some embodiments, a non-electronic tag may be applied to the consumable device 2400. In some embodiments, a non-electronic tag may comprise a barcode or other mechanism for identifying information or accessing a database that may be periodically updated. In some embodiments, the electronic tag 2750 may comprise use information, wherein said use information comprises how the consumable device 2400 has been used, including pressure experienced, flow rate used, number of uses, and solutions used.

In some embodiments, a protective film 2425 may be applied to the consumable device 2400 for transport and/or storage. This may prevent the membrane 2415 from becoming damaged or otherwise contaminated prior to use. In some embodiments, the protective film 2425 may be applied to certain portions of the consumable device 2400 in order to increase resilience or reinforce portions of the consumable device 2400 that may be subject to wear and tear as the consumable device 2400 is used.

Figure 25:
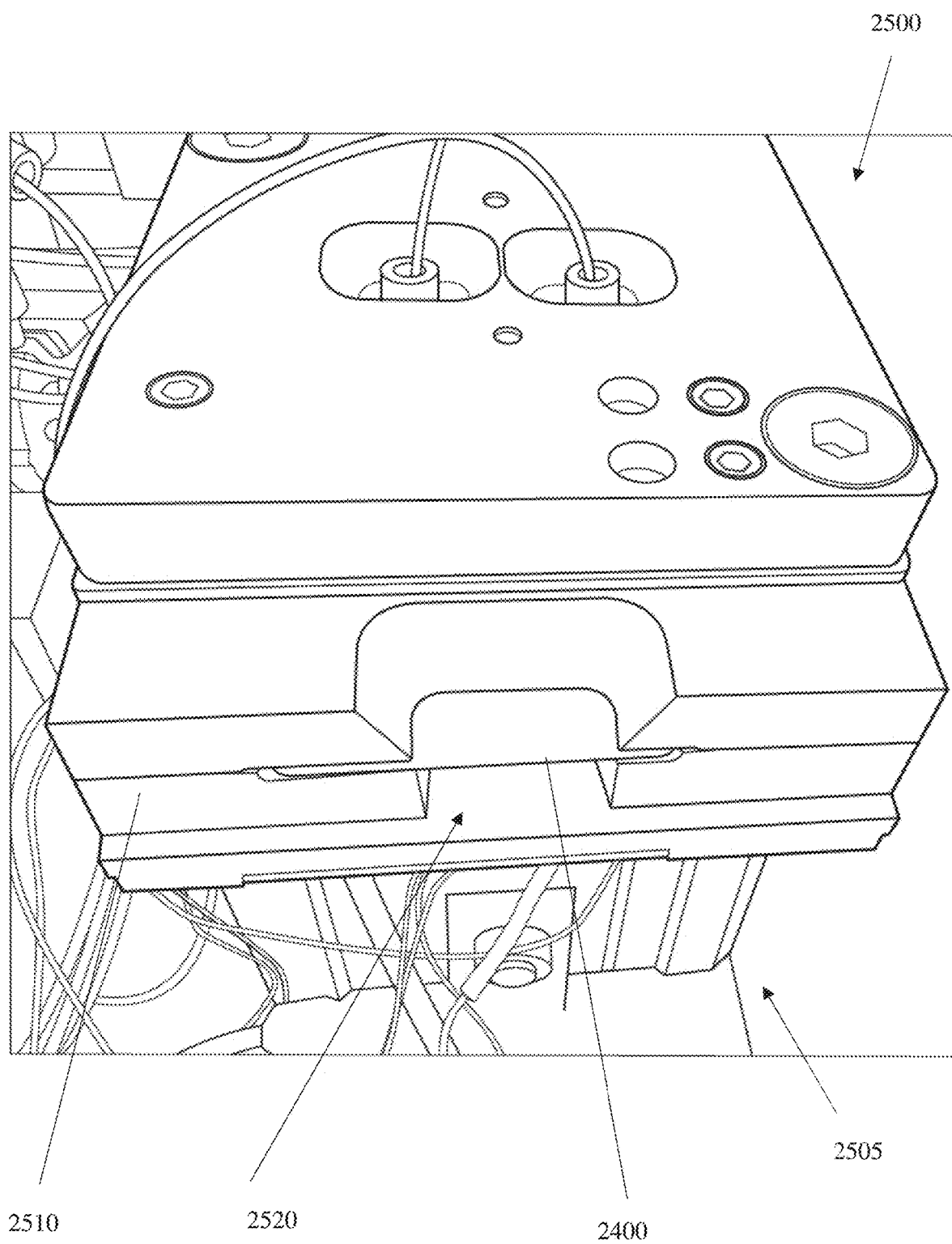
FIG. 25 is an illustration of one embodiment of a consumable device and a molecular filtration device.

FIG. 25 is an illustration of one embodiment of a consumable device 2400 and a molecular filtration device. The consumable device 2400 may be substantially similar or identical to the consumable device 2400 disclosed in FIG. 24. The molecular filtration device 2500 may be substantially similar to the molecular filtration devices disclosed hereinabove and shown in FIGS. 1-23, and further comprise additional components related to using the consumable device 2400, such that the process of engaging and disengaging the upper and lower portions of the molecular filtration device 2500 in order to properly place a membrane 2415 to create a channel is streamlined and includes certain computer automated steps.

Figure 26:
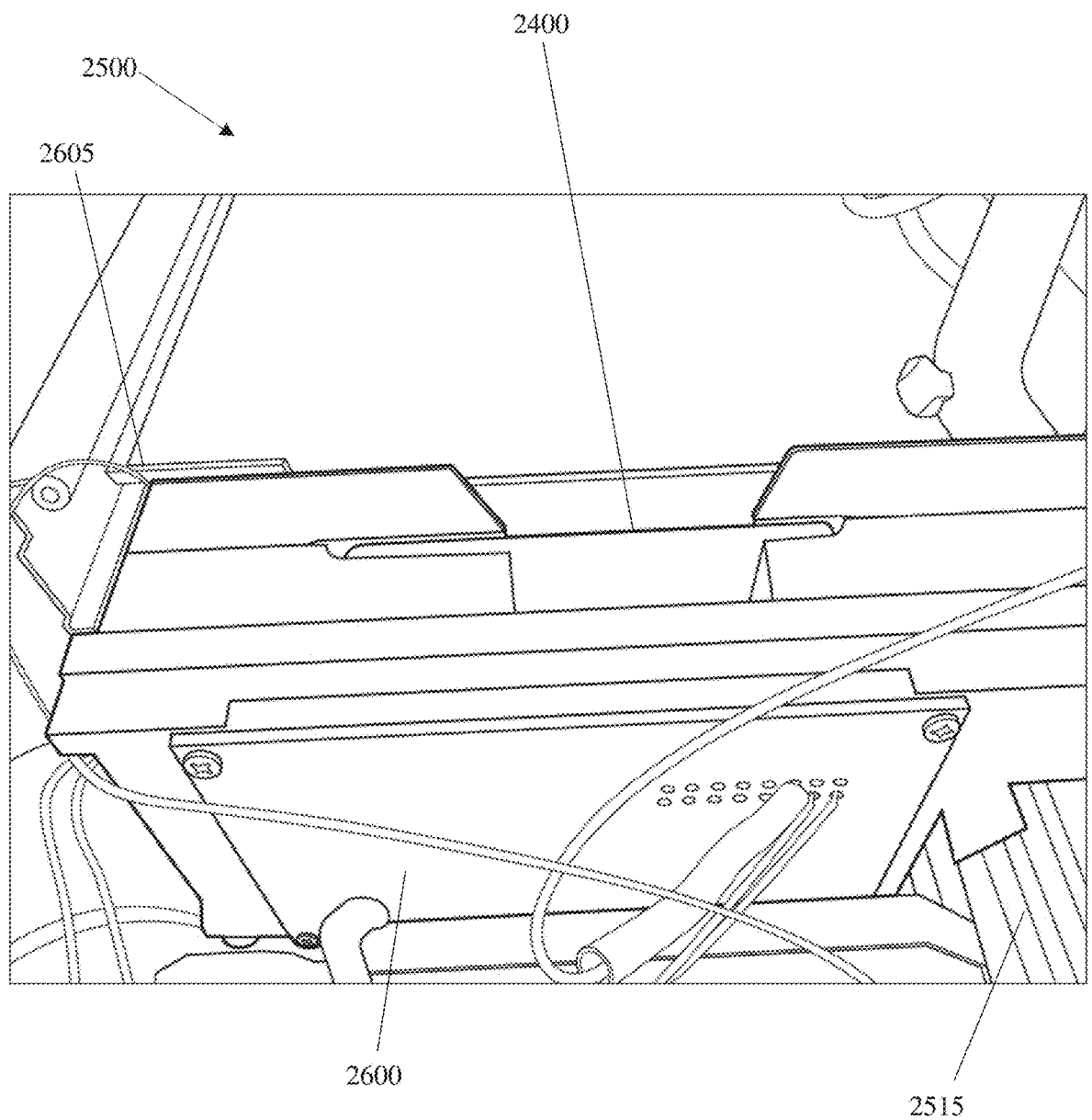
FIG. 26 is an illustration of one embodiment of a consumable device and a molecular filtration device.
Figure 29:
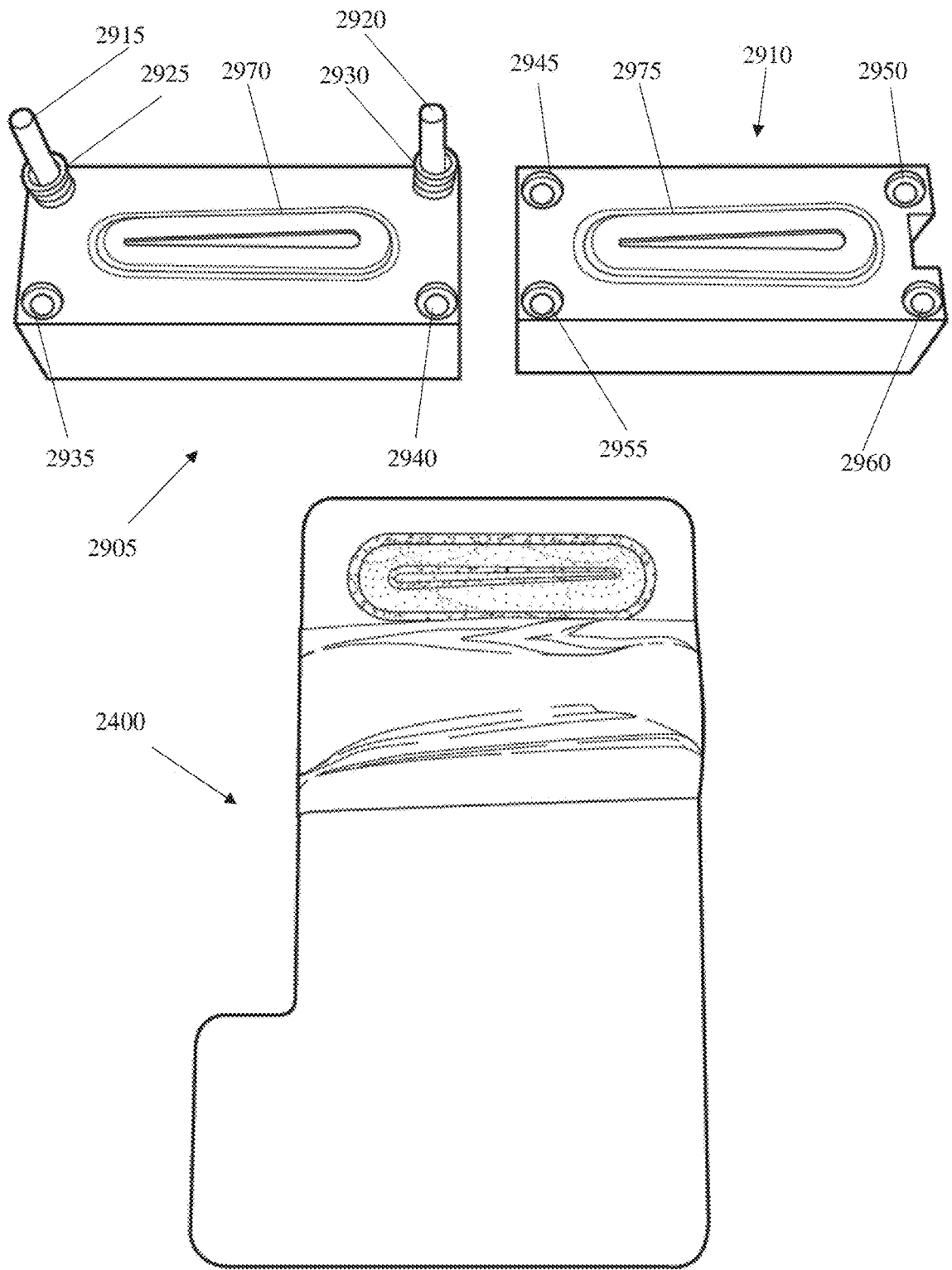
FIG. 29 is an illustration of one embodiment of a consumable device and components of a flow cell disassembled.

In some embodiments, the molecular filtration device 2500 may comprise a pneumatic sealing system 2505 configured to cause the molecular filtration device 2500 to alternate between an open and closed configuration, wherein the open configuration is when the upper and lower portions are not engaged with one another, while the closed configuration is when the upper and lower portions are engaged with one another. As shown in FIGS. 26 and 29, the pneumatic sealing system 2505 may comprise a pneumatic cylinder 2515 and biasing elements 2925, 2930.

In a preferred embodiment, when in a closed configuration, the pneumatic sealing system 2505 uses pneumatics or other pressure applying structures to apply a relatively large amount of sealing pressure on the upper and/or lower portions to cause the upper and lower portions to engage one another. In a preferred embodiment, the pneumatic sealing system 2505 may comprise biasing elements 2925, 2930, such as springs, that apply a relatively low, such as 0.1 to 3 lbs of force, and constant unsealing pressure that is configured to cause the upper and lower portions to be not engaged with one another. In one embodiment, the springs may be placed between the upper and lower portions, or within the screw, bolt, or mechanism used to align the upper and lower portions relative to one another, such that when the pneumatic sealing system 2505 is not applying the sealing pressure, the unsealing pressure is sufficient to separate the upper and lower portions from one another.

The molecular filtration device 2500 may further comprise a consumable receiving portion 2510, wherein the consumable receiving portion 2510 is configured to receive and properly orient the consumable device 2400. The consumable receiving portion 2510 may also comprise one or more sensors. The one or more sensors may be configured to read, communicate, and/or edit information contained within the electronic tag 2750 of the consumable device 2400. Additionally, the consumable receiving portion 2510 may comprise and optical light emitter and/or receiver positioned such that light emitted by the emitter is blocked from reaching the receiver when the consumable device 2400 is properly received by the consumable receiving portion 2510.

In some embodiments, the consumable receiving portion 2510 may be configured to receive the consumable device 2400 in a single and specific configuration, thereby ensuring that the membrane 2415 is properly positioned before the pneumatic sealing system 2505 applies the sealing pressure to the upper and lower portions to create the channel.

In a preferred embodiment, the pneumatic sealing system 2505 may be electronically controlled or activated, and it may be configured to apply the sealing pressure when certain requirements are met. For example, the pneumatic sealing system 2505 may be configured to apply the sealing pressure if and only if both the electronic tag 2750, as determined by the electronic sensor, indicates specific pre-identified information and the light emitted by the emitter is blocked from reaching the receiver. The fact that the light emitted is blocked may be indicative that the consumable device 2400 is properly oriented. The fact that specific information on the electronic tag 2750 is detected may be indicative that the consumable device 2400 is of a correct type for use with the molecular filtration device 2500. In some embodiments, the electronic tag 2750 may comprise information regarding the source of manufacturing of the electronic tag 2750, and use may be restricted based on characteristics therein. In some embodiments, the data contained within the electronic tag 2750 may be modified by the electronic sensor to maintain a record of how the consumable device 2400 has been used. This record of how the consumable device 2400 has been used may be beneficial to keeping track of how many times the consumable device 2400 has been used, and under what conditions the consumable device 2400 has been used. In one embodiment, if the consumable device 2400 may have been used repeatedly under relatively harsh or high pressure conditions, the sealing pressure may be prevented from being applied if it is determined that failure of the membrane 2415 may be imminent based on the record of past use.

In some embodiments, different scenarios may define parts of the record. In a first scenario, after the consumable device 2400 engages the molecular filtration device 2500, a value may be entered into the electronic tag 2750 that indicates the consumable device 2400 has been used so that the consumable device 2400 cannot be disengaged from the molecular filtration device 2500 and used again in the same or a different molecular filtration device 2500. In a second scenario, values for the maximum temperature and pressure experienced by the consumable device 2400 while in use may be entered into the electronic tag 2750 for future use. This information may be used to diagnose use issues and justify later warranty claims. In a third scenario, a maximum flowrate may be entered into the electronic tag 2750 in advance, such that the user may be unable to cause the molecular filtration device 2500 to use the consumable device 2400 at a higher flow rate than the maximum flowrate. This may prevent users from applying excess pressure to the membrane 2415 under normal operating conditions.

The pneumatic sealing system 2505 may include anchoring components 2605 to secure various components of the pneumatic sealing system 2505 to the upper and/or lower portions. Once calibrated and secured, this may allow the consumable device 2400 to easily be inserted into a correct orientation for use with the molecular filtration device 2500, such that the membrane 2415 contained within the consumable device 2400 is appropriately positioned to create a channel as disclosed hereinabove.

In some embodiments, the pneumatic sealing system 2505 may comprise a slot 2520 configured to receive and correctly position the consumable device 2400. The slot 2520 may also have cut-outs or indentations to allow a user to easily insert and remove the consumable device 2400.

It is understood that the pneumatic sealing system 2505 may be replaced with substantially any mechanism configured to apply a pressure or force.

The pneumatic sealing system 2505 may also comprise an electronic tag 2750 reader, such as an RFID PCB 2600, as shown in FIG. 26.

FIG. 26 is an illustration of one embodiment of a consumable device 2400 and a molecular filtration device 2500. The consumable device 2400 and molecular filtration device 2500 shown in FIG. 26 is the same as shown in FIG. 25.

As shown in FIG. 26, the molecular filtration device 2500 may comprise an RFID PCB reader 2600. In some embodiments, the RFID PCB reader 2600 may be replaced by substantially any device configured to read information from the electronic or other tag. In one embodiment, the RFID PCB reader 2600 may be swapped out for a barcode scanner.

FIG. 27 is an illustration of one embodiment of a stencil that may be used to assemble a consumable device. As shown in FIG. 27, the stencil 2700 may be shaped to receive a set of complementary layers 2705, 2706 that may be combined to form, for example, the consumable device 2400. Each of the layers 2705, 2706 may comprise a window 2710, 2711 and tab 2720, as shown in FIG. 24. In one embodiment, the first layer 2705 may be placed within the stencil 2700, and the second layer 2706 may then be placed on top. In one embodiment, a membrane, adhesive, and RFID tag 2750 may be placed in suitable locations before the second layer 2706 is put in the stencil 2700 and on top of the first layer 2705. Preferably, the stencil 2700 securely orients both layers 2705, 2706 relative to one another. In this embodiment, a user may place specific membranes and specific RFID tags to best suit their needs at the time. This may also allow the user to place additional components between the two layers 2705, 2706 as needed. The stencil 2700 may be referred to as a fixture, jig, or other name intended to identify the stencil 2700 as a physical structure useful for aligning layers 2705, 2706 and components of the consumable device 2400.

Figure 28:
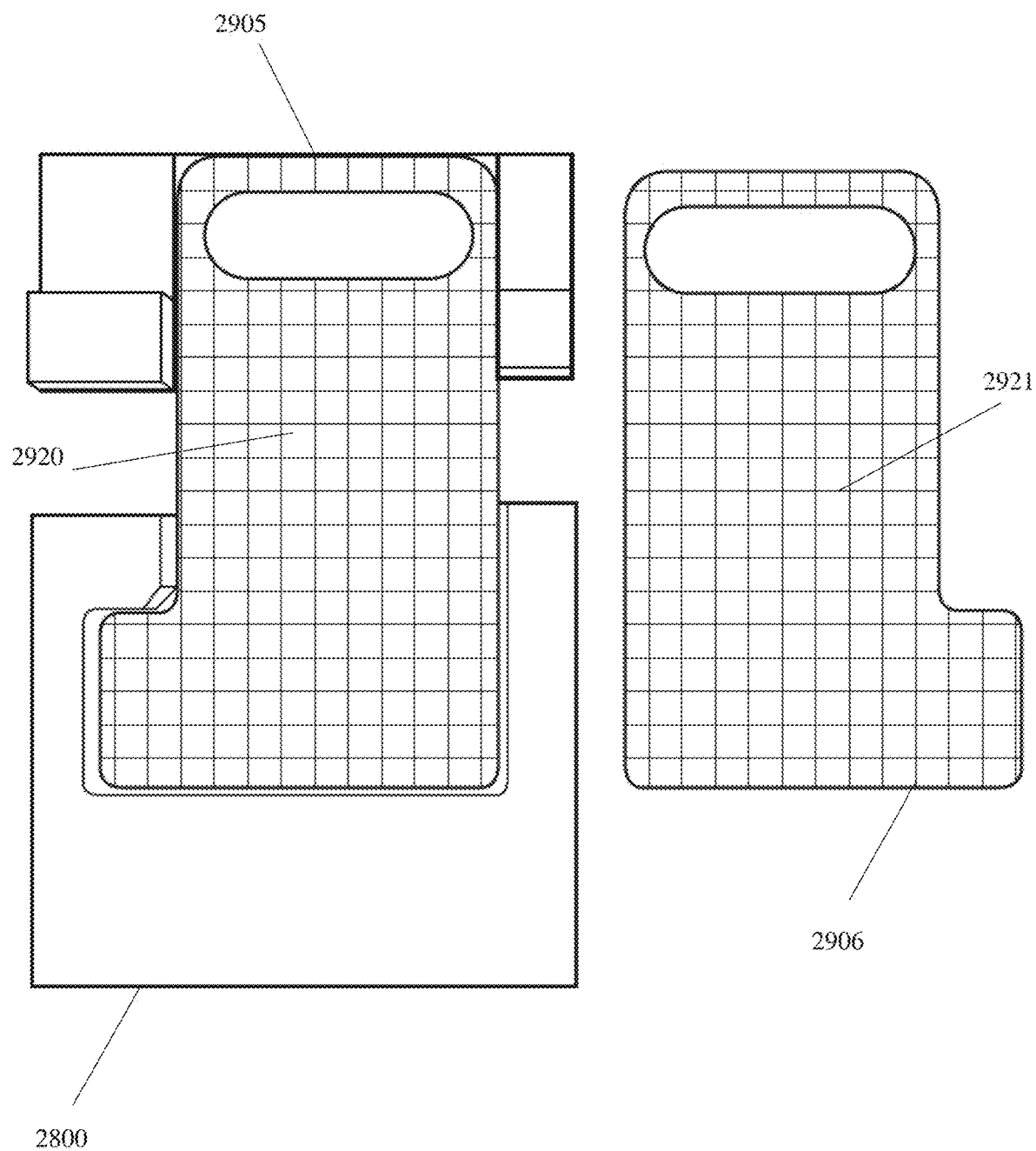
FIG. 28 is an illustration of one embodiment of a stencil that may be used to assemble a consumable device.

FIG. 28 is an illustration of one embodiment of a stencil that may be used to assemble a consumable device. As shown in FIG. 28, the stencil 2800 may be configured to receive two or more layers 2905, 2906, each layer 2905, 2906 having adhesive on complementary surfaces, wherein the adhesive is protected by a removable film 2920, 2921 prior to combining the two layers 2905, 2906. In one embodiment, the film 2920, 2921 may be removed to expose the adhesive, and then the two layers 2905, 2906 may be combined (and thus secured adhesively together) using the stencil 2800. In some embodiments, the two layers 2905, 2906 may be combined without a stencil.

FIG. 29 is an illustration of one embodiment of a consumable device and components of a flow cell disassembled. As shown in FIG. 29, upper 2970 and lower sealing 2975 surfaces may be similar in size and/or shape as the window 2410 and portion of membrane 2415 (shown in FIG. 24) that is exposed through the window 2410. In some embodiments, the only portion of the consumable device 2400 that must physically contact the molecular filtration device 2500 in order to function as intended, excluding the pneumatic sealing system 2505, is the membrane 2415.

The molecular filtration device 2500 may have upper 2905 and lower portions 2910, and it may ensure proper alignment by having alignment pins 2915, 2920 engage alignment holes 2945, 2950, 2955, 2960, 2935, 2940 present on the opposite portions. In one embodiment, the alignment pins 2915, 2920 may include a biasing element 2925, 2930, such as a spring, such that when a pressure of force that holds the upper 2905 and lower portions 2910 together is released, the biasing element 2925, 2930 causes the upper 2905 and lower portions 2910 to push away from each other and disengage.

In different embodiments, the alignment pins 2915, 2920 may be located in different locations or different alignment holes, such that the location of the alignment pins 2915, 2920 may be adjusted for different use scenarios, such as a consumable device that is configured to engage the upper 2970 and lower sealing 2975 surfaces from a different side. In some embodiments, the alignment pins 2915, 2920 may block proper engagement of the consumable device, and may having the alignment pins 2915, 2920 modular or movable, the alignment pins 2915, 2920 may be adjusted to not block proper engagement of the consumable device. In some embodiments, a subset of the alignment holes may be 2945, 2950, 2955, 2960, 2935, 2940 unused.

The consumable device 2400 shown in FIG. 29, is shown after being properly inserted and secured within the flow cell, which is why the shape of the flow cell appears on the membrane 2415. The pressure from the flow cell engaging the membrane 2415 may affect the membrane 2415 surface.

In order for the consumable device 2400 to be properly received by and engaged with the flow cell to create the channel, the sealing pressure must be applied evenly along the sealing surfaces of the upper and lower portions of the flow cell. In one embodiment, the sealing pressure is applied evenly by having a pressure shaft that is decoupled from the flow cell stabilizing apparatus such that the pressure shaft "floats" relative to the flow cell, thereby self-leveling.

Figure 30:
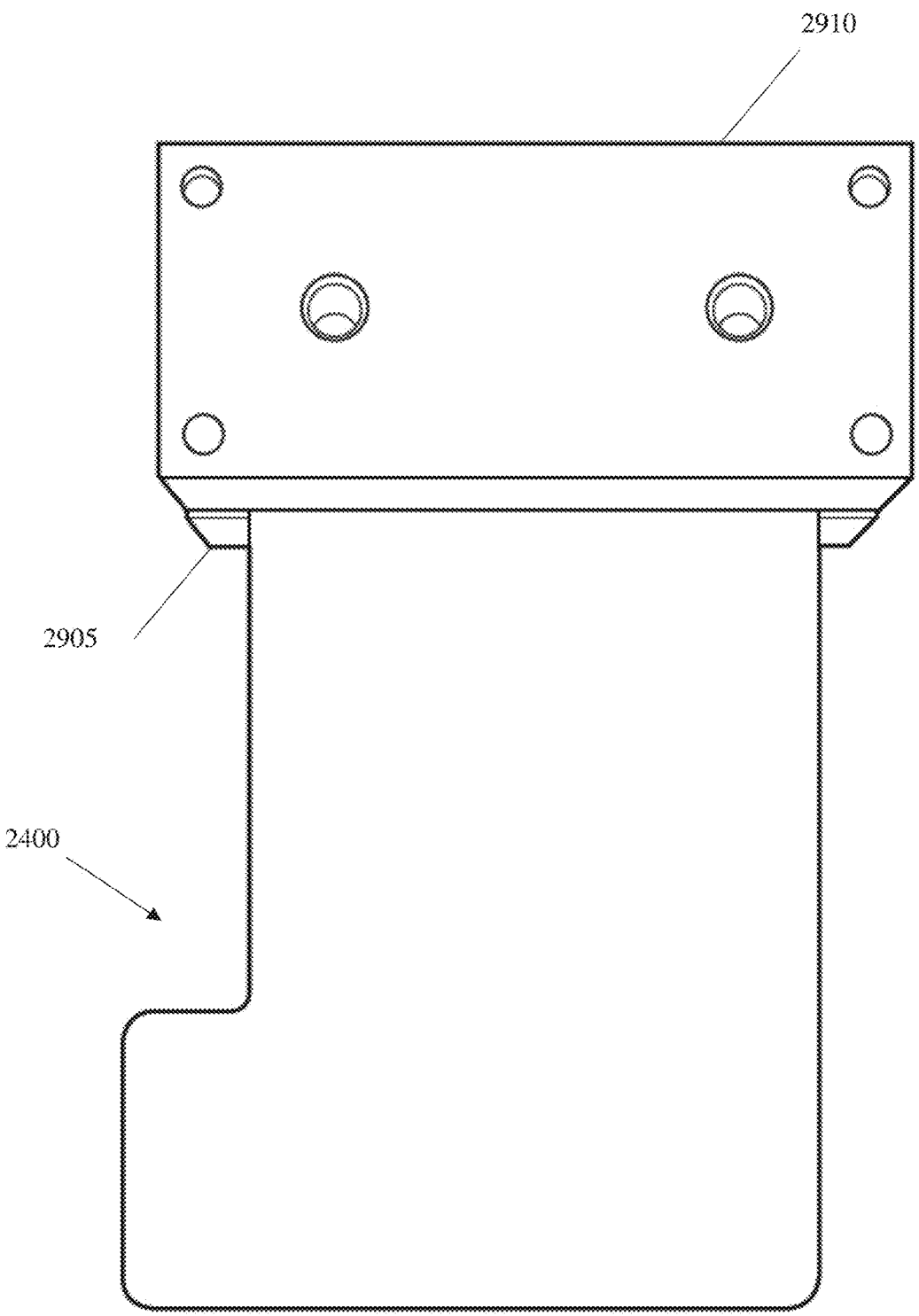
FIG. 30 is an illustration of one embodiment of a consumable device engaged with a flow cell.

FIG. 30 is an illustration of one embodiment of a consumable device 2400 engaged with a flow cell, wherein the flow cell comprises the upper 2905 and lower portions 2910.

Figure 31:
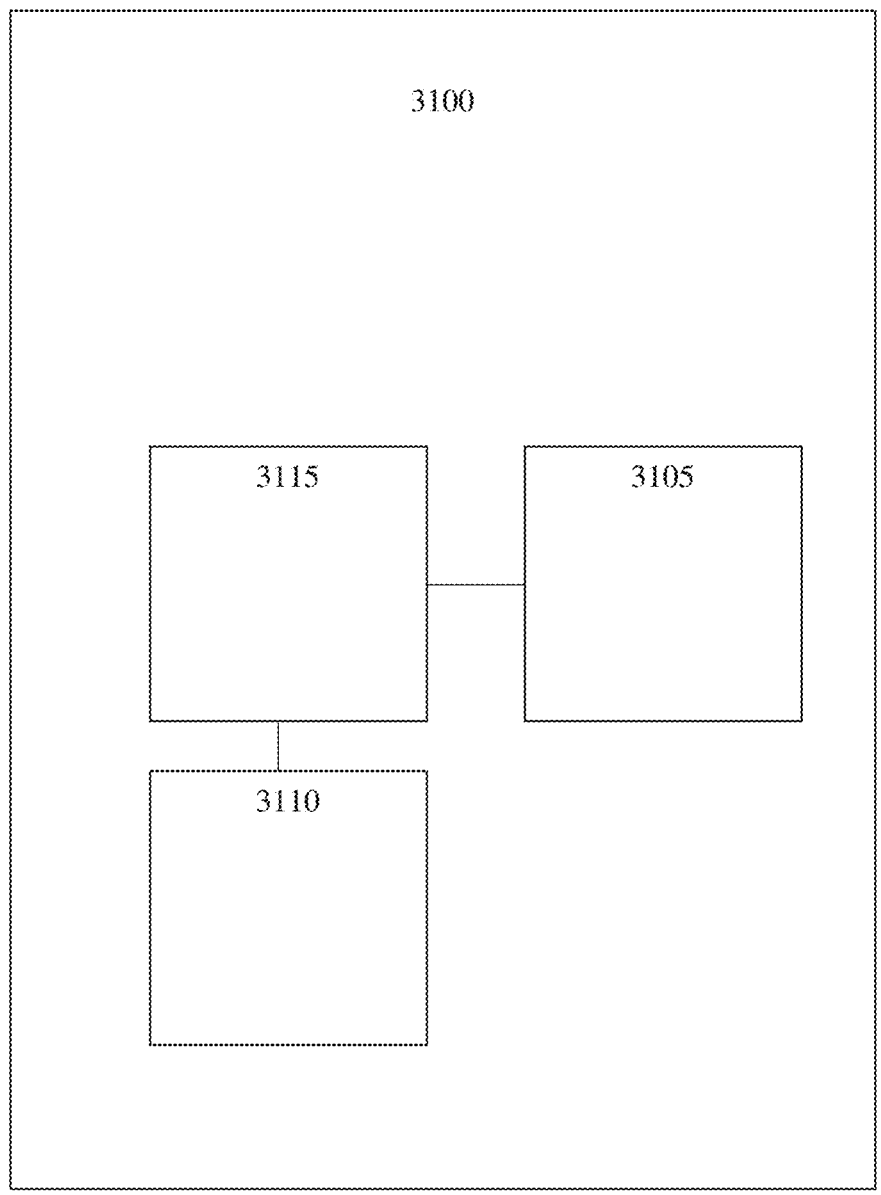
FIG. 31 is a block diagram of one embodiment of a molecular filtration device.

FIG. 31 is a block diagram of one embodiment of a molecular filtration device. As shown in FIG. 31, the molecular filtration device 3100 may comprise a sensor 3105, pneumatic system control module 3110 and a communication module 3115. The molecular filtration device 3100 may be substantially similar to the molecular filtration devices described hereinabove. The sensor 3105 may be configured to scan or read information stored on a consumable device 2400, whether the information is stored on the consumable device 2400 electronically or physically. The sensor 3105 may be configured to communicate the information to the communication module 3115, which may in turn transmit the collected information to a computer, either onboard the molecular filtration device or physically separate. If physically separate, the communication module 3115 may be configured to transmit the information wired or wirelessly to the computer for analysis. The computer may be configured to analyze the information and depending on the information, the computer may send a signal to the communication module 3115 such that a signal may be sent to the pneumatic system control module 3110, which may be configured to actuate a pneumatic sealing system described hereinabove.

In some embodiments the sensor 3105 may include the ability to write information onto an electronic tag contained within the consumable device. In this embodiment, the communication module 3115 may receive information about the process used with the molecular filtration device and cause the sensor 3115 to write or record that information onto the electronic tag. This may aid in record keeping.

Figure 32:
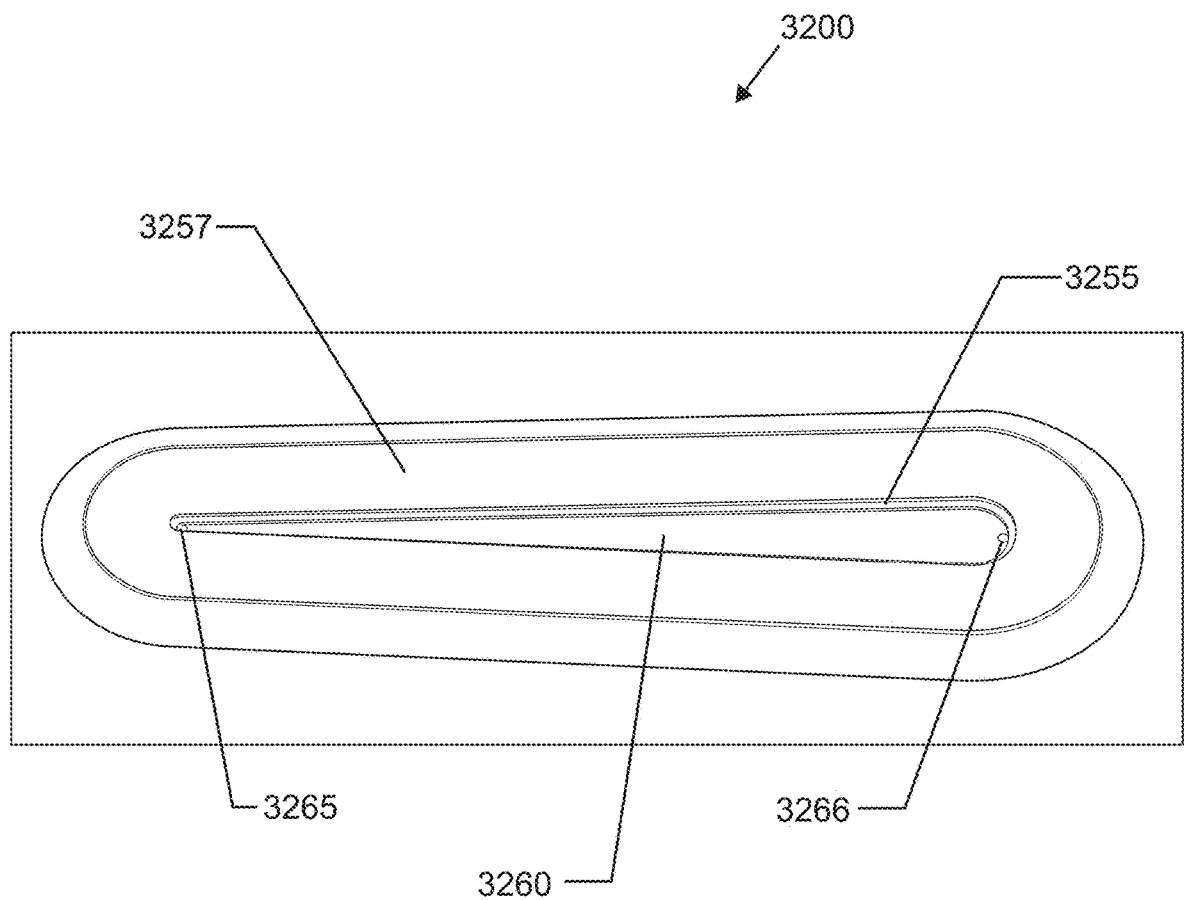
FIG. 32 is an illustration of a top view of one embodiment of a lower portion showing dual drain ports.

FIG. 32 is an illustration of a top view of one embodiment of a lower portion showing dual drain ports. As shown in FIG. 32, the lower portion 3200 may comprise an upper sealing surface 3257, a first lower hole 3265, a second lower hole 3266, a frit supporting lip 3255, and reservoir 3260.

In some embodiments, the lower portion 3200 may be configured to be a replacement for lower portions 150, 2100, wherein the upper sealing surface 3257, frit supporting lip 3255, and reservoir 3260 function substantially similarly or identically to corresponding components.

One difference between the upper sealing surface 3257 of lower portion 3200 as compared to the upper sealing surfaces 157, 2157 of lower portions 150, 2100 is that the upper sealing surface 3257 is raised relative to the top surface of the lower portion 3200. The upper sealing surface 3257 being raised relative to the top of the lower portion 3200 may be beneficial when the lower portion 3200 is being used in a molecular filtration system configured to accept the consumable device 2400 shown in FIG. 24. One reason the upper sealing surface 3257 being raised may be beneficial because in some embodiments, the membrane 2415 of the consumable device 2400 may be sandwiched between the first and second layers 2905, 2906 of the consumable device, such that the membrane's 2415 surface may be depressed relative to the first and second layers 2905, 2906. Accordingly, the upper sealing surface 3257 being raised may allow the upper sealing surface 3257 to come into contact with the membrane 2415 directly, rather than the first or second layers 2905, 2906 of the consumable device 2400.

The first and second lower ports 3265, 3266 may be configured to receive lower flow devices configured to inject or withdraw solution from the reservoir 3260. As used herein, the terms inject and withdraw do not necessarily denote the mechanism for causing flow of solution, but rather are used to denote the direction of flow of solution.

In one embodiment, the first lower hole 3265 may be configured to inject solution or buffer into the reservoir 3260, while the second lower hole 3266 may be configured to withdraw solution from the reservoir 3260. When the first lower hole 3265 and second lower hole 3266 work in tandem in this way, the combination may increase overall flow of solution through the molecular filtration device and prevent buildup of material or air bubbles within the reservoir.

In some embodiments, the lower portion 3200 may be a suitable replacement for not only lower portions 150, 2100, but also a replacement for upper portions 105, 865, such that two lower portions 3200 may engage one another, with appropriate modifications, in order to create a molecular filtration device. One benefit of utilizing two lower portions 3200 for this purpose is that both lower portions 3200 may provide stabilizing structures, similar to the frit supporting lip 3255 in order to provide a frit supporting structure on both faces of the membrane. This may also allow additional geometries to be effectively used for the channels, such as channel 920, and shown in FIGS. 8A-C.

Figure 33:
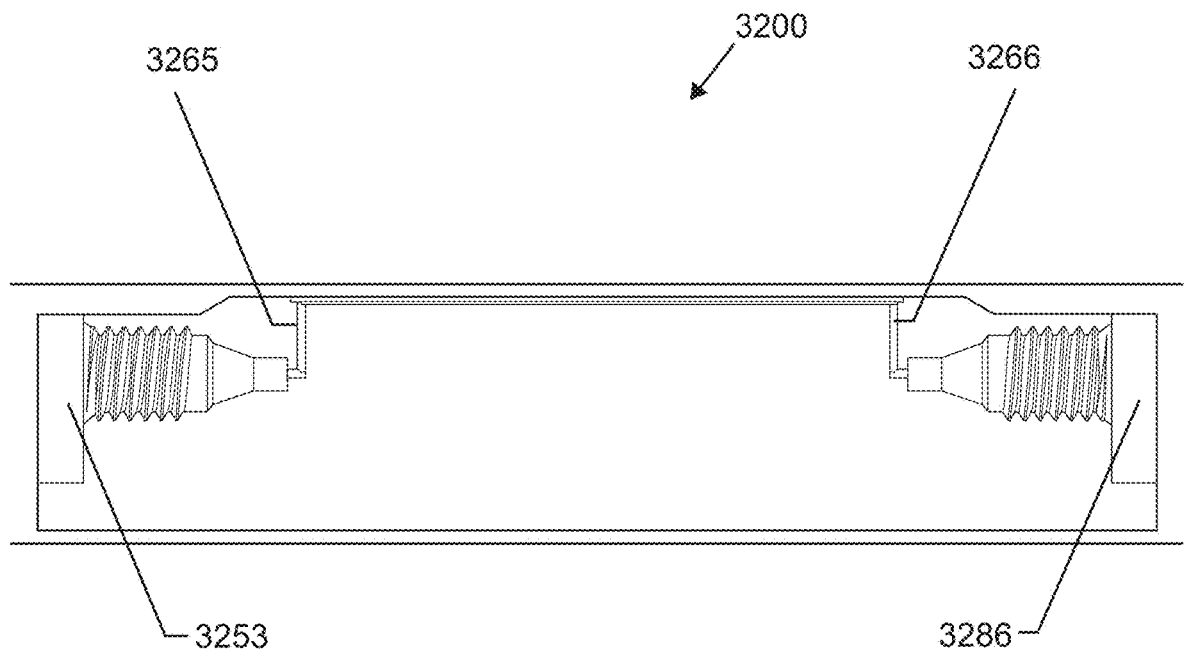
FIG. 33 is an illustration of a cross section side view of one embodiment of a lower portion showing dual drain ports.

FIG. 33 is an illustration of a cross section side view of one embodiment of a lower portion showing dual drain ports. As shown, the lower portion 3200 may comprise a first drain port 3285 and a second drain port 3286. The first drain port 3285 may be configured to allow solution to flow to or from the first lower hole 3265. The second drain port 3286 may be configured to allow solution to flow to or from the second lower hole 3266. The first and second drain ports 3285, 3286 may be substantially flat in relation to the lower portion 3200, such that if corresponding inlet ports of an upper portion are also flat, and this upper portion is used with the lower portion 3200, the resulting molecular filtration device may be stacked with other similarly configured molecular filtration devices and the multiple molecular filtration devices may be used in tandem, as shown in FIG. 34.

Figure 34:
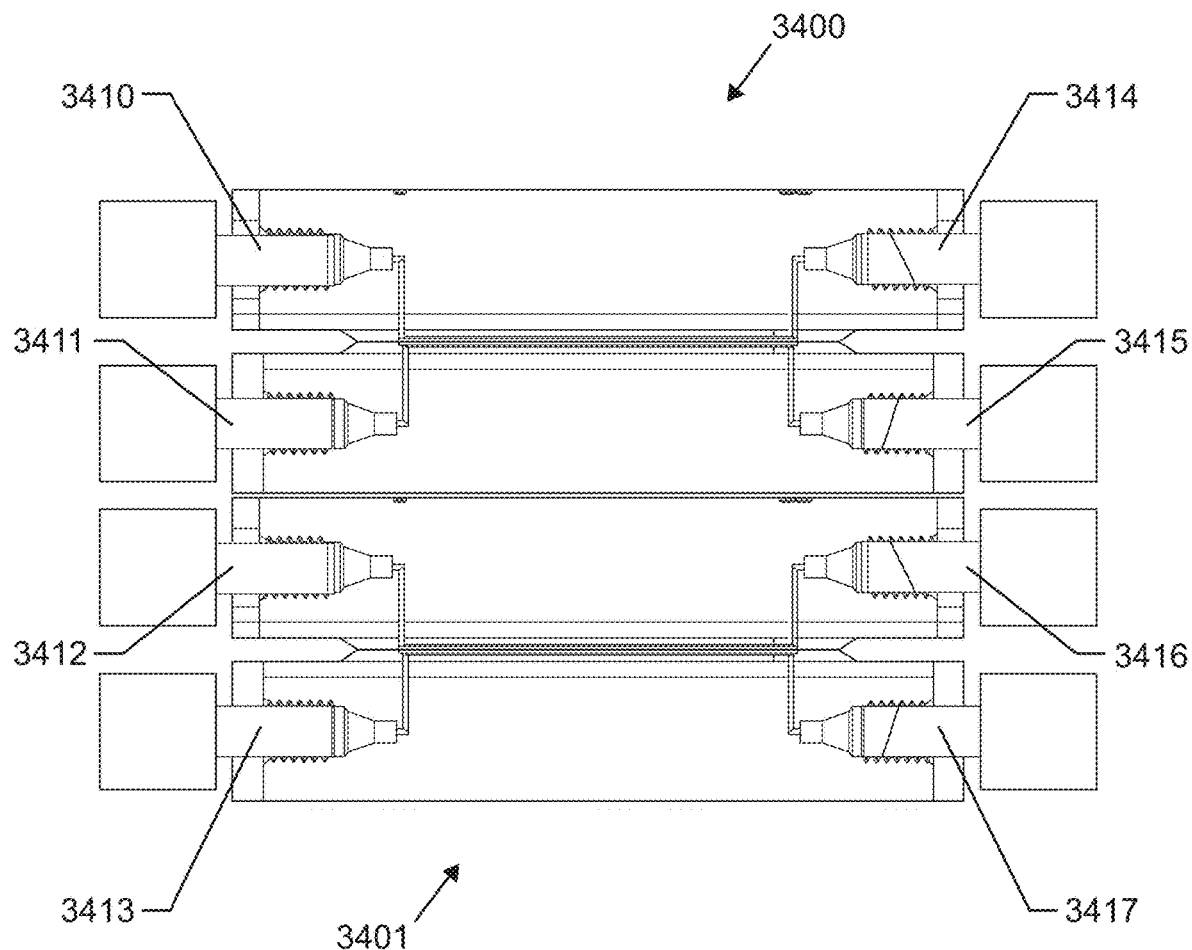
FIG. 34 is an illustration of a cross section side view of two molecular filtration devices in a stacked configuration.

FIG. 34 is an illustration of a cross section side view of two molecular filtration devices in a stacked configuration. As shown in FIG. 34, the two molecular filtration devices 3400, 3401 may comprise inlet and drain ports 3410, 3411, 3412, 3413, 3414, 3415, 3416, 3417 that are flat relative to the molecular filtration devices 3400, 3401. In this way, the two molecular filtration devices 3400, 3401 may be used in a single application and a single structure may be used to engage lower and upper portions of the molecular filtration devices 3400, 3401.

One advantage of having the two molecular filtration devices 3400, 3401 in a stacked configuration is that each molecular filtration device 3400, 3401 may have a membrane with a different molecular weight cut-off, thereby allowing for different size molecules to be isolated in each of the two molecular filtration devices 3400, 3401. For example, the first molecular filtration device 3400 may have a membrane with a larger molecular weight cutoff than a membrane in the second molecular filtration device 3401. In this way, the second molecular filtration device 3401 may be able to isolate molecules that pass through the larger molecular weight cutoff membrane and not the smaller molecular weight cutoff membrane.

Figure 35:
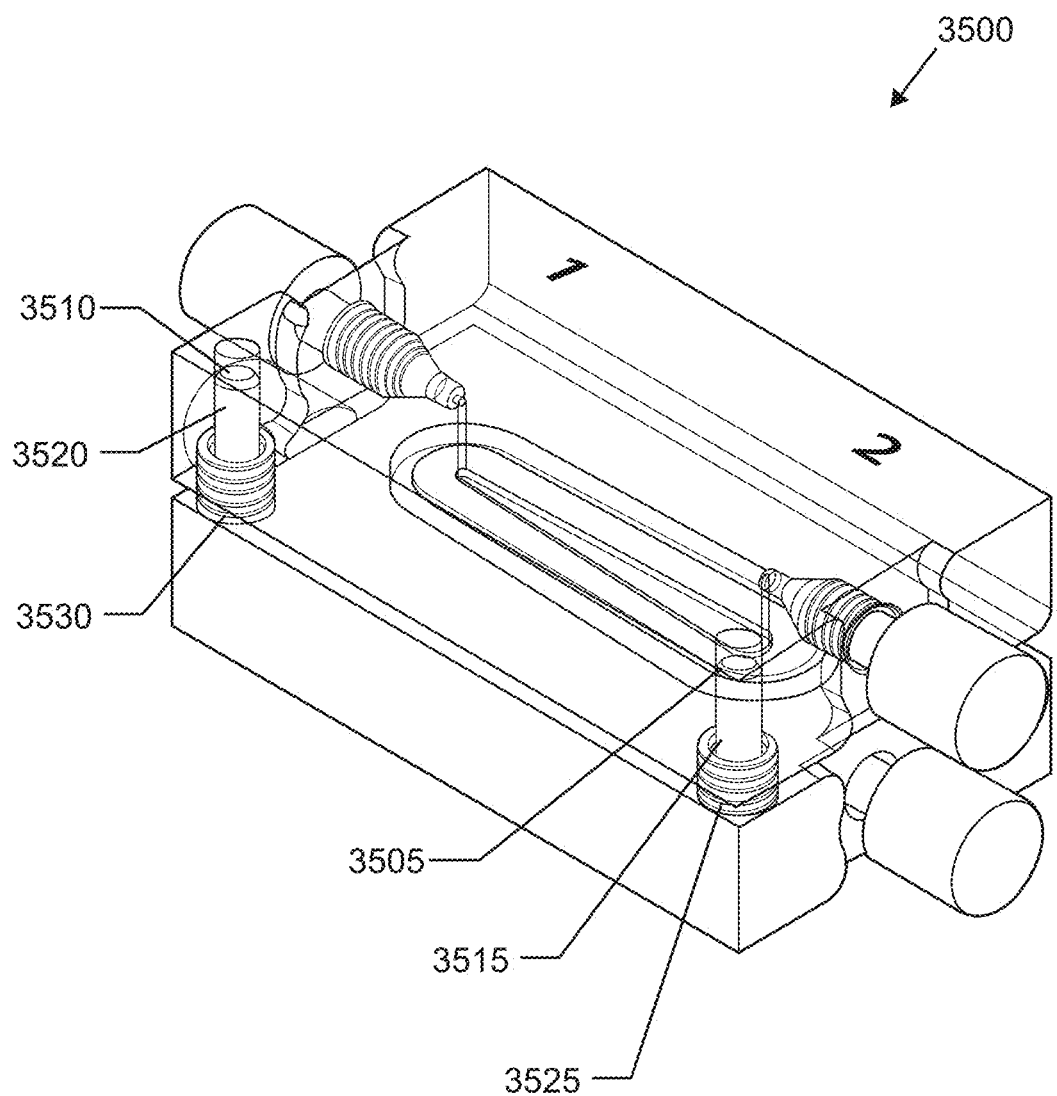
FIG. 35 is a transparent perspective illustration of a molecular filtration device having flat ports.

FIG. 35 is a transparent perspective illustration of a molecular filtration device having flat ports. As shown in FIG. 34, the molecular filtration device 3500 may comprise alignment holes 3505, 3510, alignment pins 3515, 3520, and alignment springs 3525, 3530. In a preferred embodiment, the alignment holes 3505, 3510, alignment pins 3515, 3520, and alignment springs 3525, 3530, may be located on one side of the molecular filtration device 3500, rather than on opposite sides. This configuration may be preferable so that the consumable device 2400 may be able to engage the sealing surfaces of the lower portion and upper portion without being blocked or impeded by the alignment pins 3515, 3520 or alignment springs 3525, 3530.

The foregoing description of the preferred embodiment has been presented for the purposes of illustration and description. While multiple embodiments are disclosed, still other embodiments will become apparent to those skilled in the art from the above detailed description. These embodiments are capable of modifications in various obvious aspects, all without departing from the spirit and scope of protection. Accordingly, the detailed description is to be regarded as illustrative in nature and not restrictive. Also, although not explicitly recited, one or more embodiments may be practiced in combination or conjunction with one another. Furthermore, the reference or non-reference to a particular embodiment shall not be interpreted to limit the scope of protection. It is intended that the scope of protection not be limited by this detailed description, but by the claims and the equivalents to the claims that are appended hereto.

Except as stated immediately above, nothing that has been stated or illustrated is intended or should be interpreted to cause a dedication of any component, step, feature, object, benefit, advantage, or equivalent, to the public, regardless of whether it is or is not recited in the claims.

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those of ordinary skill in the art that various modifications and variations may be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A molecular filtration device comprising:
an upper portion; and
a lower portion;
wherein said upper portion comprises two upper ports;
wherein said two upper ports comprise a first upper port and a second upper port;
wherein said first upper port is configured to receive a first upper flow device;
wherein said second upper port is configured to receive a second upper flow device;
wherein said first upper flow device is configured to alternate between injecting and not injecting solution;
wherein said second upper flow device is configured to alternate between injecting and withdrawing solution;
wherein said lower portion comprises one or more lower ports and a reservoir;
wherein said one or more lower ports are configured to receive one or more lower flow devices;
wherein said lower flow devices are configured to alternate between injecting and withdrawing solution from said reservoir;
wherein said upper portion comprises a channel forming lip;
wherein a channel forming cavity is formed by said channel forming lip when said upper portion and said lower portion are engaged;
wherein a lower sealing surface of said upper portion and an upper sealing surface of said lower portion are configured to receive and compress a membrane; and
wherein a channel is defined by said channel forming cavity and said membrane.

2. The molecular filtration device of claim 1, wherein said membrane is a filtration membrane.

3. The molecular filtration device of claim 2, wherein said filtration membrane is a molecular weight cut off filtration membrane.

4. The molecular filtration device of claim 1, wherein said upper sealing surface of said lower portion and said lower sealing surface of said upper portion are configured to apply a pressure to one another through said membrane.

5. The molecular filtration device of claim 1, wherein said upper sealing surface of said lower portion is raised relative to a top surface of said lower portion.

6. The molecular filtration device of claim 1, wherein said upper ports and said one or more lower ports are oriented horizontally relative to said upper portions and lower portions, respectively.

7. The molecular filtration device of claim 1, wherein said one or more lower ports comprise a first lower port and a second lower port.

8. The molecular filtration device of claim 1, further comprising an upper rigid support member configured to be received within said channel forming lip in order to provide structural support to an upper surface of said membrane.

9. The molecular filtration device of claim 1, wherein said channel forming cavity is teardrop shaped.

10. The molecular filtration device of claim 1, wherein said channel forming cavity is oval shaped.

11. The molecular filtration device of claim 1, wherein said channel forming cavity is elongated rectangle shaped.

12. The molecular filtration device of claim 1, wherein said upper portion and said lower portion are configured to matingly engage one another.

13. The molecular filtration device of claim 1, further comprising one or more alignment pins and one or more alignment holes;
wherein said one or more alignment holes are configured to receive said one or more alignment pins.

14. The molecular filtration device of claim 13, wherein said one or more alignment pins are located on said lower portion and said one or more alignment holes are located on said upper portion.

15. The molecular filtration device of claim 14, further comprising one or more biasing elements that are configured to engage said one or more alignment pins and apply a force that is configured to separate said lower and upper portions.

16. The molecular filtration device of claim 14, wherein said alignment holes and said alignment pins are located on a single side of said lower and upper portions.

17. A molecular filtration device comprising:
an upper portion; and
a lower portion;
wherein said upper portion comprises two upper ports;
wherein said two upper ports comprise a first upper port and a second upper port;
wherein said first upper port is configured to receive a first upper flow device;
wherein said second upper port is configured to receive a second upper flow device;
wherein said first upper flow device is configured to alternate between injecting and not injecting solution;
wherein said second upper flow device is configured to alternate between injecting and withdrawing solution;
wherein said lower portion comprises one or more lower ports and a reservoir;
wherein said one or more lower ports are configured to receive one or more lower flow devices;
wherein said lower flow devices are configured to alternate between injecting and withdrawing solution from said reservoir;
wherein said upper portion comprises a channel forming lip;
wherein a channel forming cavity is formed by said channel forming lip when said upper portion and said lower portion engage one another;

wherein a lower sealing surface of said upper portion and an upper sealing surface of said lower portion are configured to receive and compress a membrane;

wherein a channel is defined by said channel forming cavity and said membrane;

wherein said membrane is a molecular weight cut off filtration membrane;

wherein said upper sealing surface of said lower portion and said lower sealing surface of said upper portion are configured to apply a pressure to one another through said membrane;

wherein said upper sealing surface of said lower portion is raised relative a top surface of said lower portion;

wherein said upper ports and said one or more lower ports are oriented horizontally from said upper portions and lower portions, respectively;

wherein said one or more lower ports comprise a first lower port and a second lower port;

wherein said lower portion and upper portion comprise one or more alignment pins and one or more alignment holes;

wherein said one or more alignment holes are configured to receive said one or more alignment pins;

wherein said one or more alignment pins are located on said lower portion and said one or more alignment holes are location on said upper portion; and wherein said one or more alignment holes and said one or more alignment pins are located on a single side of said lower and upper portions.

\* \* \* \* \*